US010465165B2

(12) United States Patent
Cho et al.

(10) Patent No.: US 10,465,165 B2
(45) Date of Patent: Nov. 5, 2019

(54) GROWTH MATRICES FOR STEM CELL PROPAGATION IN VITRO AND IN TISSUE REGENERATION

(71) Applicants: Rutgers, The State University of New Jersey, New Brunswick, NJ (US); New Jersey Institute of Technology, Newark, NJ (US)

(72) Inventors: Cheul Cho, Whippany, NJ (US); Steven Levison, Cedar Grove, NJ (US); Nolan Skop, Succasunna, NJ (US); Frances Calderon, Livingston, NJ (US); Chirag Gandhi, Mamaroneck, NY (US)

(73) Assignees: RUTGERS, THE STATE UNIVERSITY OF NEW JERSEY, New Brunswick, NJ (US); NEW JERSEY INSTITUTE OF TECHNOLOGY, Newark, NJ (US)

(*) Notice: Subject to any disclaimer, the term of this patent is extended or adjusted under 35 U.S.C. 154(b) by 181 days.

(21) Appl. No.: 14/763,944

(22) PCT Filed: Jan. 28, 2014

(86) PCT No.: PCT/US2014/013381
§ 371 (c)(1),
(2) Date: Jul. 28, 2015

(87) PCT Pub. No.: WO2014/117146
PCT Pub. Date: Jul. 31, 2014

(65) Prior Publication Data
US 2015/0361395 A1 Dec. 17, 2015

Related U.S. Application Data

(60) Provisional application No. 61/757,378, filed on Jan. 28, 2013.

(51) Int. Cl.
C12N 5/0797 (2010.01)
A61K 35/28 (2015.01)
(Continued)

(52) U.S. Cl.
CPC .......... *C12N 5/0623* (2013.01); *A61K 9/0085* (2013.01); *A61K 9/5078* (2013.01);
(Continued)

(58) Field of Classification Search
None
See application file for complete search history.

(56) References Cited

U.S. PATENT DOCUMENTS

2010/0254900 A1* 10/2010 Campbell ............... A61L 27/18
424/1.65
2011/0104052 A1  5/2011 Barnett et al.
2012/0282324 A1* 11/2012 Xing ................. A61K 38/1825
424/450

FOREIGN PATENT DOCUMENTS

WO  2008/072230   6/2008
WO  2011/156586  12/2011
(Continued)

OTHER PUBLICATIONS

International Search Report and Written Opinion dated Apr. 25, 2014, issued in Application No. PCT/US2014/013381.
(Continued)

*Primary Examiner* — Erin M. Bowers
(74) *Attorney, Agent, or Firm* — Fox Rothschild LLP

(57) ABSTRACT

The present invention provides a multifunctional 2-D and 3-D matrix for propagation of stem cells. In particular, a chitosan-based biomaterial scaffold is engineered to promote CNS regeneration from primitive neural precursors by stabilizing a recombinant protein, fibroblast growth factor to preserve the cardinal properties of stem cells. The matrix, is
(Continued)

further modified by the addition of either the extracellular matrix protein fibronectin or the small peptide RGD or IKVAV. A method to manufacture an injectable multifunctional microsphere scaffold is also disclosed that is suitable as a vehicle for cell transplantation to repair traumatic brain injuries.

19 Claims, 12 Drawing Sheets

Specification includes a Sequence Listing.

(51) Int. Cl.
| | | |
|---|---|---|
| A61K 35/51 | (2015.01) | |
| A61K 35/545 | (2015.01) | |
| C12N 5/00 | (2006.01) | |
| A61K 9/00 | (2006.01) | |
| A61K 9/50 | (2006.01) | |
| A61K 35/30 | (2015.01) | |

(52) U.S. Cl.
CPC .............. *A61K 35/28* (2013.01); *A61K 35/30* (2013.01); *A61K 35/51* (2013.01); *A61K 35/545* (2013.01); *C12N 5/0068* (2013.01); *C12N 2501/115* (2013.01); *C12N 2533/52* (2013.01); *C12N 2533/72* (2013.01)

(56) References Cited

FOREIGN PATENT DOCUMENTS

| WO | WO 2011/156586 | * 12/2011 |
|---|---|---|
| WO | 2012/087965 | 6/2012 |
| WO | 2012/119012 | 9/2012 |

OTHER PUBLICATIONS

Evans, G.R., "Challenges to nerve regeneration" Semin Surg Oncol, 2000, vol. 19, issue 3, pp. 312-318 (Abstract only).

Guimond et al., "Highly diverse heparan sulfate analogue libraries: a novel resource for bioactivity screening of proteins" Int J Exp Pathol, 2004, vol. 85, issue 4, pp. A62-A63 (Abstract only).

Ma et al., "Transplantation of neural stem cells enhances expression of synaptic protein and promotes functional recovery in a rat model of traumatic brain injury," Mol. Med Rep, 2011, vol. 4, pp. 849-856.

Salman et al., "Subventricular zone neural stem cells remodel the brain following traumatic injury in adult mice" J. Neurotrauma, 2004, vol. 21, issue 3, pp. 283-292 (Abstract only).

Sanberg et al., "Neurological disorders and the potential role for stem cells as a therapy" Br Med Bull, 2012, vol. 101, pp. 163-181.

Shear et al., "Neural progenitor cell transplants promote long-term functional recovery after traumatic brain injury" Brain Res, 2004, vol. 1026, issue 1, pp. 43-51 (Abstract only).

Shindo et al., "Differences in the neuronal stem cells survival, neuronal differentiation and neurological improvement after transplantation of neural stem cells between mild and severe experimental traumatic brain injury" J. Med Invest, 2006, vol. 53, issue 1-2, pp. 42-51.

Sun et al., "Basic fibroblast growth factor-enhanced neurogenesis contributes to cognitive recovery in rats following traumatic brain injury" Exp Neurol, 2009, vol. 216, issue 1, pp. 56-65.

Tate et al., "Laminin and fibronectin scaffolds enhance neural stem cell transplantation into the injured brain" J. Tissue Eng Regen Med, 2009, vol. 3, issue 3, pp. 208-217 (Abstract only).

Moore, et al: "Tethered Growth Factors on Biocompatible Scaffolds Improve Stemness of Cultured Rat and Human Neural Stem Cells and Growth of Oligodendrocyte Progenitors", 2018, Methods, vol. 133, pp. 54-64.

* cited by examiner

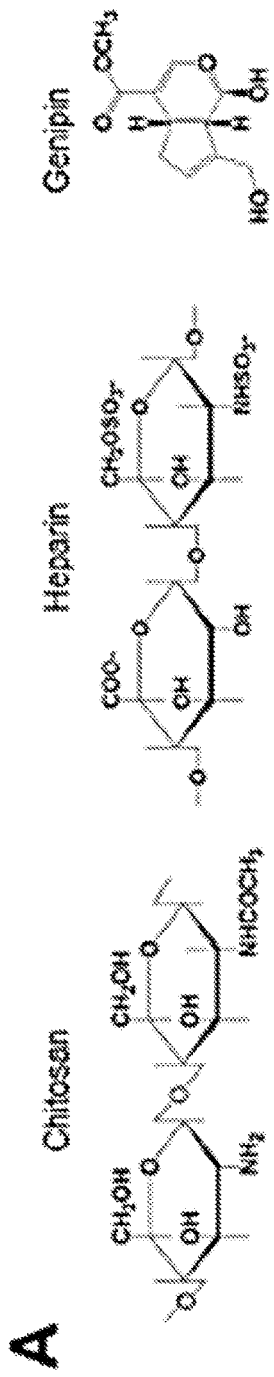
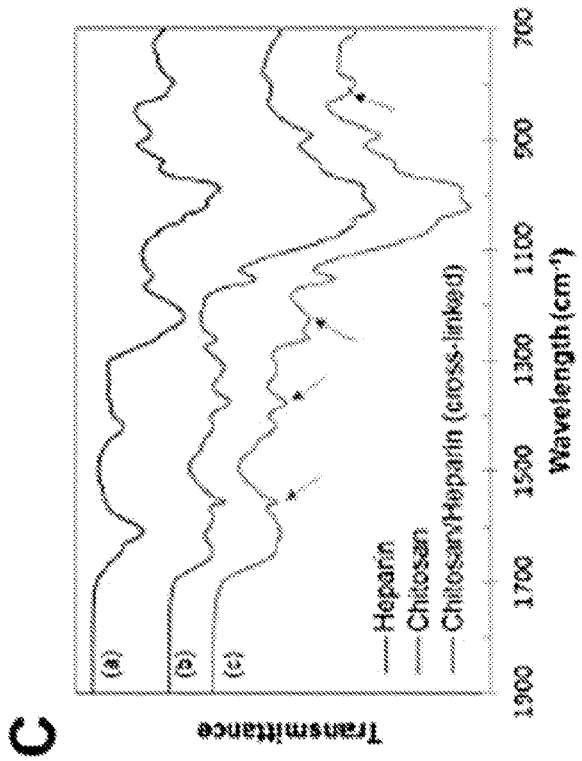
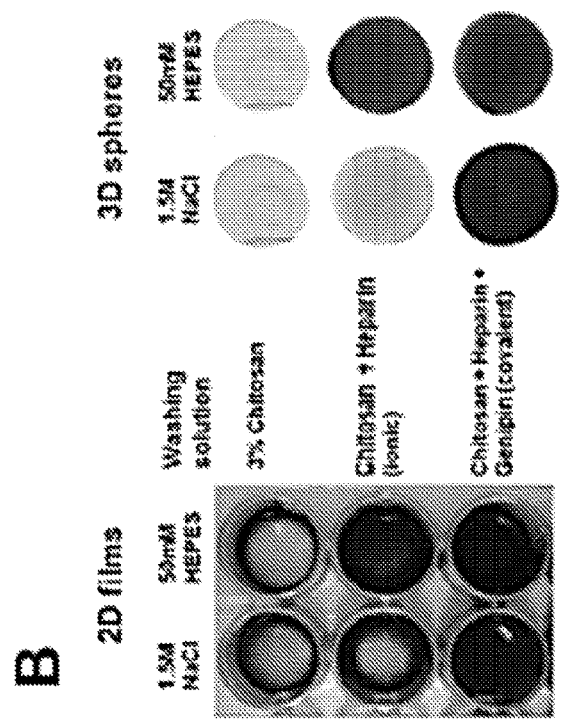
FIG. 6A
FIG. 6B
FIG. 6C

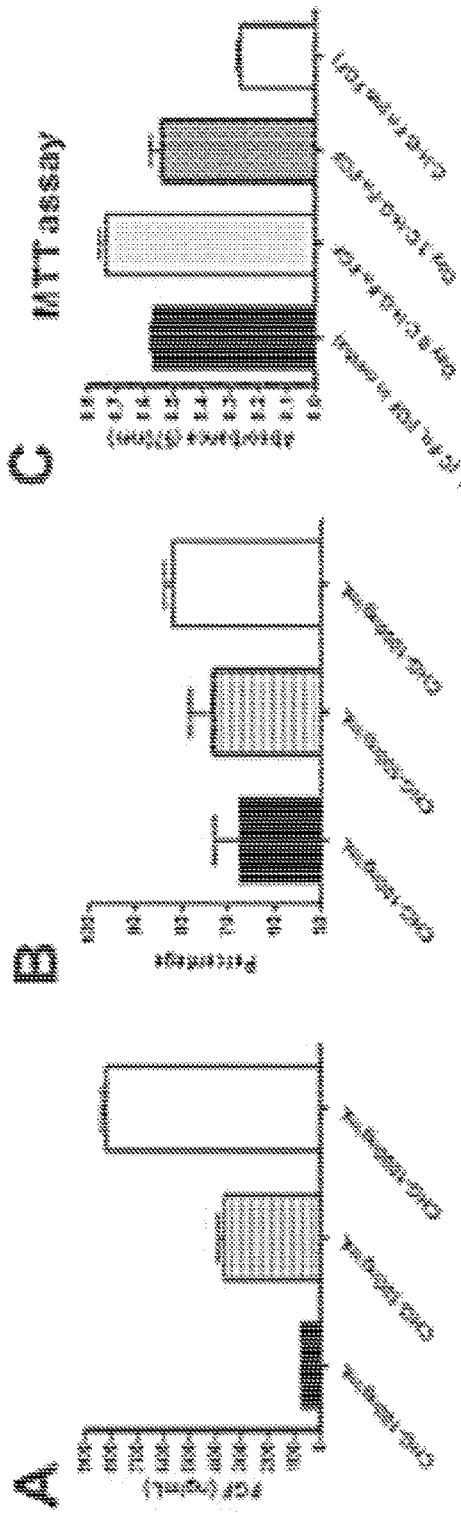
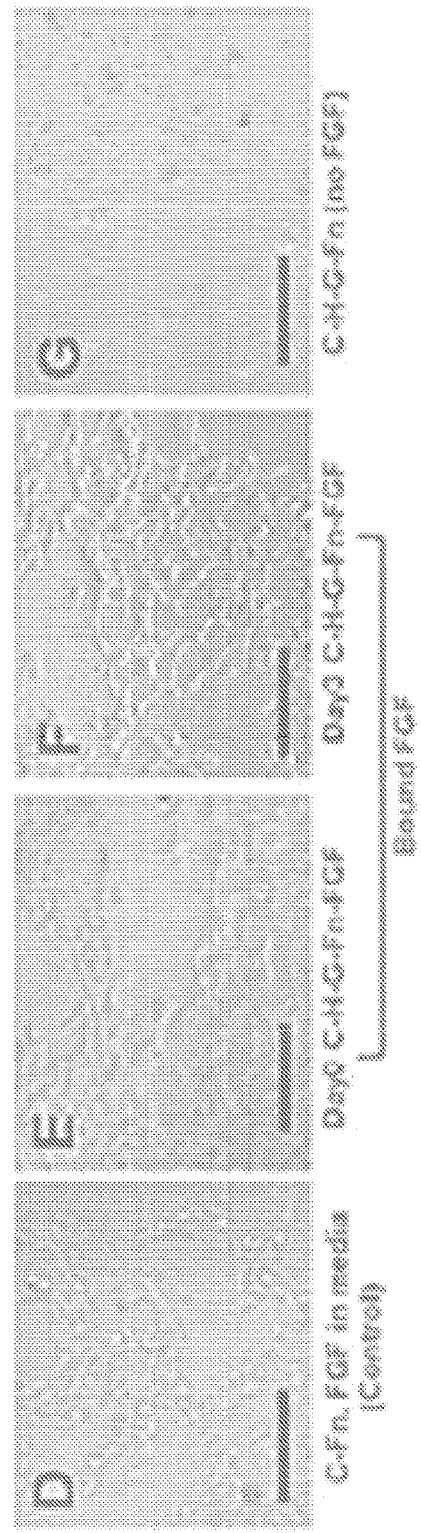

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ile Lys Val Ala Val
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Arg Gly Asp Ser
1

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Gly Arg Gly Asp Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Gly Arg Gly Asp Ser Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Gly Arg Gly Asp Thr Pro
1               5

<210> SEQ ID NO 6
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MeGly
<222> LOCATION: (1)..(1)

<400> SEQUENCE: 6

Gly Arg Gly Asp Ser Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Gly Arg Gly Asp Ser Pro Lys
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Arg Gly Asp Ser Pro Ala Ser Ser Lys Pro
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Ala Cys Asp Cys Arg Gly Asp Cys Phe Cys Gly
1               5                   10

<210> SEQ ID NO 10
<211> LENGTH: 19
<212> TYPE: PRT
<213> ORGANISM: Artificial Sequence
<220> FEATURE:
<223> OTHER INFORMATION: Synthetic

<400> SEQUENCE: 10

Cys Ser Arg Ala Arg Lys Gln Ala Ala Ser Ile Lys Val Ala Val Ser
1               5                   10                  15

Ala Asp Arg

<210> SEQ ID NO 11
<211> LENGTH: 19
<212> TYPE: PRT
<213> ORGANISM: Artificial Sequence
<220> FEATURE:
<223> OTHER INFORMATION: Synthetic
```

```
<400> SEQUENCE: 11

Cys Ser Arg Ala Arg Lys Gln Ala Ala Ser Ile Lys Val Ala Val Ser
1               5                   10                  15

Ala Asp Arg
```

GROWTH MATRICES FOR STEM CELL PROPAGATION IN VITRO AND IN TISSUE REGENERATION

CROSS-REFERENCE TO RELATED APPLICATION

The present application is the U.S. National Phase of International Patent Application Serial No. PCT/US14/13381, filed Jan. 28, 2014 which claims the benefit of priority under 35 U.S.C. § 119(e) of U.S. Provisional Application Ser. No. 61/757,378, filed Jan. 28, 2013. The entire disclosures of the applications noted above are incorporated herein by reference.

STATEMENT OF GOVERNMENT SUPPORT

The present invention was made with government support under contracts 09-3207-BIR-E-2 and CBIR12FEL025 awarded by the New Jersey Commission on Brain Injury Research.

FIELD OF THE INVENTION

This invention relates generally to a field of tissue engineering. In particular, the present invention relates to the stabilization of a recombinant protein, fibroblast growth factor 2 (FGF-2), to promote its biological activity on stem cells and a method for culturing stem cells.

BACKGROUND

Stem cell therapeutics is a promising field for tissue engineering and regeneration but it has shown limited success in repairing the central nervous system (CNS) and specifically the brain after severe injury. CNS injuries often cause extensive tissue damage characterized by neuronal and glial cell death where there is virtually no functional replacement of cells from the endogenous neural stem cells (NSCs). In an animal model of stroke, it was reported that less than 1% of the destroyed neurons are replaced from the endogenous neural precursors of the subventricular zone (SVZ). Similar results have been obtained in animal models of traumatic brain injury (TBI). Salman et al. (*J Neurotrauma* 21: 283-292, 2004) observed that neural precursors (NPs) from the SVZ repopulated a mechanically injured cortex. The SVZ cells proximal to the injured area produced a very small percentage of new neurons (not quantified), with the majority of the transplanted cells becoming astrocytes. Direct transplantation of NPs into the penumbra of brain lesions has yielded minor advancements (Sanberg et al., *Br Med Bull* 101: 163-181, 2012). Most of the transplanted cells either do not survive (Shindo et al., *J Med Invest* 53: 42-51, 2006) or differentiate into glial cells instead of neurons (Shear et al., *Brain Res* 1026: 11-22, 2004). Shear et al. (2004), for example, found that NG2 positive glial cells were produced upon transplanting NPs and Sun et al. (*Exp Neurol* 216: 56-65, 2011) observed that the majority of the precursors they transplanted became Olig2 positive cells (presumably glia). Ma et al. (*Mol Med Rep* 4: 849-856, 2011) reported that only 4% of NPs that they transplanted were NSCs, whereby only 11% differentiated into cells expressing a neuronal marker. Transplanting stem cells attached to a supportive matrix directly into the lesion site may be more effective in promoting regeneration. Tate et al. (*J Tissue Eng Regen Med* 3: 208-217, 2009) showed improvement in the long-term survival of NPs that were transplanted within a supportive fibronectin and laminin matrix after TBI. Animals receiving these transplants also showed improved performance in spatial learning tasks compared with injured mice that did not receive NPs (Tate et al., 2009).

Using principles from material engineering and molecular biology, tissue engineers are developing organic substitutes to support or replace portions of malfunctioning tissues or organs to create substitutes. The common approach to create these substitutes is to use living cells, scaffolding and signaling molecules. Evans (*Semin Surg Oncol* 19: 312-318, 2000) identified four components necessary for nervous tissue scaffolds: growth-promoting proteins, extracellular matrix (ECM), support cells (typically stem cells) and molecules that will promote axonal regeneration. However, stem cells require both contact with extracellular matrices as well as growth-promoting proteins to proliferate and retain the cardinal characteristics of stem cells (stemness). Extracellular matrix factors such as laminin and fibronectin, acting through integrin receptors, have been shown to be important for stem cell self-renewal. Of the growth growth-promoting proteins necessary for stimulating the proliferation of both embryonic and somatic stem cells, FGF-2 has been shown to be critical.

Traumatic injuries to the CNS are appropriate for the application of biomaterial scaffolds because there is extensive and localized loss of cells and ECM. A scaffold can serve as an artificial matrix and supportive network for engrafted cells as well as for the host tissue. Furthermore, it serves as both a physical and chemical barrier against glial scarring, which is well known to inhibit axonal regeneration. The ECM is also an important regulator of cell function. Interactions of ECM and integrins govern cellular processes such as proliferation, survival, migration and differentiation.

There is, therefore, a continuing need when designing regenerative therapies for neural tissue to develop biomaterial systems that mimic the native ECM. Such biomaterial systems should be designed in order to achieve a scaffold that is highly suitable as a vehicle for cell transplantation to repair traumatic brain injuries.

SUMMARY

In view of the above-described problems, needs, and goals the inventors have devised embodiments of the present invention in which a plurality of stem cells can be maintained on 2-D and 3-D matrices that have been modified to stabilize growth-promoting proteins within them. As such, these matrices (or biomaterial scaffolds) can be deployed, for example, to promote CNS regeneration.

In one exemplary embodiment, a method of entering a population of stem cells relies upon immobilizing fibroblast growth factor (FGF) to a surface of a culture plate. The method generally has the steps of: (i) coating a bottom of a chamber with a chitosan solution; (ii) drying the chitosan solution to form a chitosan layer: (iii) neutralizing the acidity of the chitosan layer; (iv) binding a heparin to the chitosan layer; (v) cross-linking the heparin to the chitosan layer using genipin; (vi) binding a growth-promoting protein; (vii) applying a solution of an adhesive component (e.g., extracellular matrix protein or extracellular matrix peptide); (viii) binding the adhesive component to the chitosan, which creates a multifunctional film; and (ix) seeding the population of stem cells onto the chamber and culturing the stem cells. The method can also have washing/rinsing steps between the additions of each component. In a preferred embodiment, the growth-promoting protein is one or more growth factors, such as fibroblast growth factor-2 (FGF-2). Without being bound by theory, stem cells plated onto the disclosed multifunctional matrix remain in a multipotent and proliferative state without providing soluble growth-promoting proteins. Moreover, the stem cells can remain less mature and more highly proliferative than cells maintained on a fibronectin-coated substrate in a culture medium supplemented with soluble growth-promoting proteins, such as FGF-2.

The cultured stem cells using the disclosed method are highly suitable for cell transplantation to repair tissue damage, such as traumatic brain injury. In one embodiment, the present invention provides a method to repair injured mammalian tissue by administration of a multifunctional matrix into a subject in need of treatment. The multifunctional matrix comprises a chitosan-(genipin)-growth-promoting protein binding partner, an immobilized thereon growth factor, preferably FGF-2, alone or in combination with an adhesive component. In one embodiment, the adhesive component is fibronectin. In another embodiment, the adhesive component is a peptide sequence arginine-glycine-aspartic acid (RGD) or isoleucinc-lysine-valine-alanine-valine (IKVAV).

In an exemplary embodiment, the multifunctional matrix is provided having a scaffold with immobilized FGF-2, heparin, genipin and chitosan. In another exemplary embodiment, the multifunctional matrix is provided having a scaffold of chitosan, genipin-linked heparin with immobilized FGF-2 and fibronectin.

In one embodiment, a method to manufacture an injectable multifunctional microsphere scaffold is provided to achieve a scaffold that is highly suitable as a vehicle for cell transplantation to repair traumatic CNS injuries. In an exemplary embodiment, to serve as a vehicle for cell transplantation, a chitosan solution is electrosprayed into a coagulation bath to generate microspheres (range: 30-100 μm) that can be subsequently modified. Primitive neural precursors seeded onto the multifunctional microspheres can be propagated in culture, and the microspheres containing cells are small enough to be injected using a 26 gauge Hamilton syringe into the region of the CNS that had previously sustained a contusion injury. Thus, this multifunctional scaffold can be used as a cellular and growth factor delivery vehicle to promote the regeneration of nervous tissue injury after CNS injuries.

The preferred methods and materials are described below in examples which are meant to illustrate, not limit, the invention. Skilled artisans will recognize methods and materials that are similar or equivalent to those described herein, and that can be used in the practice or testing of the present invention. Unless otherwise defined, all technical and scientific terms used herein have the same meaning as commonly understood by one of ordinary skill in the art to which this invention belongs. Other features and advantages of the invention will be apparent from the detailed description and from the claims.

BRIEF DESCRIPTION OF THE DRAWINGS

FIG. 6: Ionic and covalent immobilization of heparin on the 2D chitosan films and 3D microspheres. (A) Structures of chisotan, heparin, and fibronectin. (B) Heparin immobilization onto chitosan coated well ionically and covalently using genipin. Stained with toluidine blue dye. (C) FT-IR spectra of heparin, chitosan, and genipin cross-linked chitosan-heparin complex. Arrows indicate functional groups for heparin and chitosan from the genipin cross-linked chitosan-heparin complex.

FIG. 7: FGF-2 binding and neural stem cell culture on the genipin cross-linked chitosan-heparin complex films. (A) Bound FGF-2 amount at different concentration. (B) Efficiency of bound FGF-2 at different concentration. (C) MTT assay on various substrate conditions. (D-G) Morphology of the neural stem cells on the various substrates. Scale bars: 100 µm.

DETAILED DESCRIPTION OF THE INVENTION

Figure 1A:
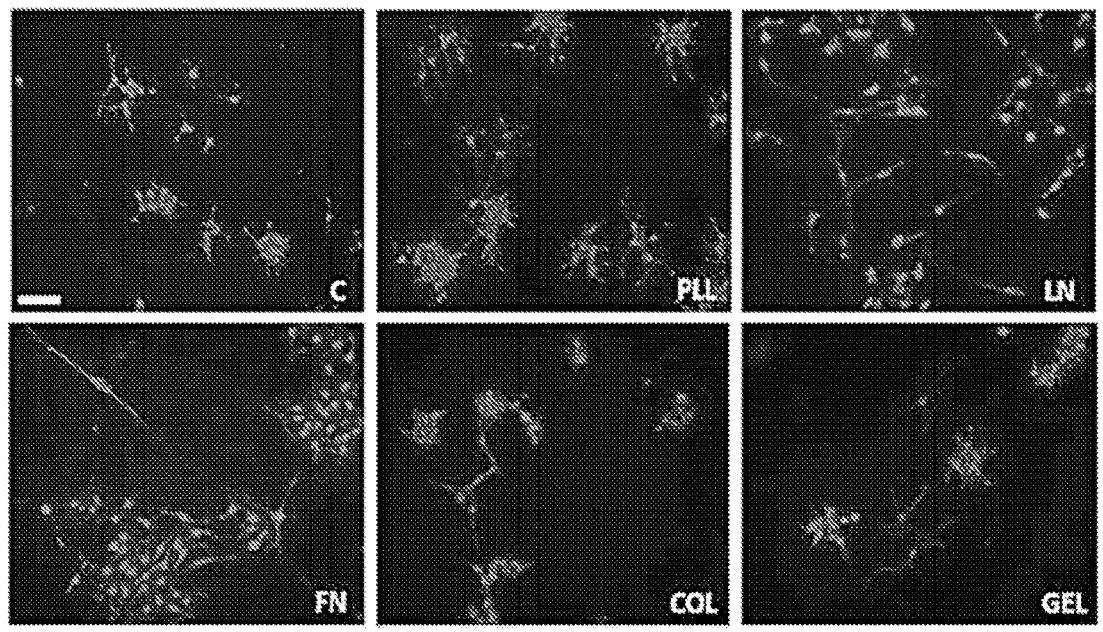
FIG. 1: Substrate effect on morphology and proliferation of RG3.6 cells. RG3.6, a neural stem cell line, was grown in DMEM/F12 supplemented with B27 and 10 ng/ml FGF-2 daily for 5 days. Cells stained with F-actin and DAPI. Process length from nucleus was measured using Sigma Scan Pro. Process numbers from nucleus were counted manually. Error bars indicate SEM. Statistical significance as determined by ANOVA with Tukey's post hoc. (A) RG3.6 cells grown on chitosan coated dishes with various adsorbed peptides, 20× magnification. Ln: Laminin, Fn: Fibronectin, Gel: Gelatin, PLL: Poly-L-lysine, Col: Collagen, C: Control (chitosan alone) (B) *=p<0.001 vs. control and ◆◆◆=p<0.001 vs laminin and gelatin. (C) *p<0.001 vs. PLL and control, *=p<0.05 vs. PLL and control, and ◆◆=p<0.01 vs laminin collagen and gelatin. D) Cells were stained with nuclear antibodies Ki67 and DAPI. Scale bar, 100 μm.
Figure 1B:
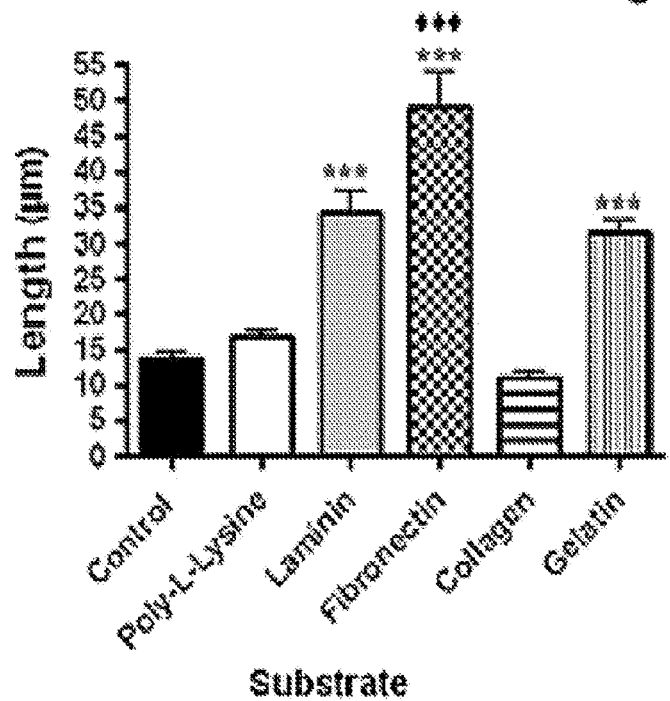
Figure 1C:
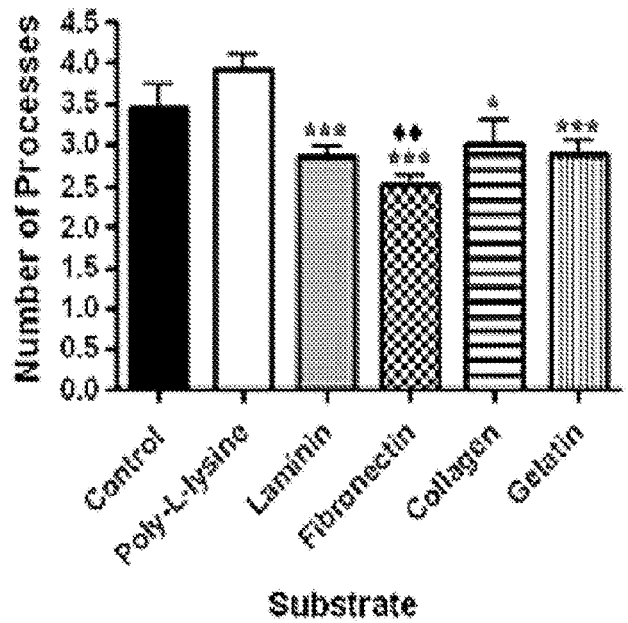
Figure 1D:
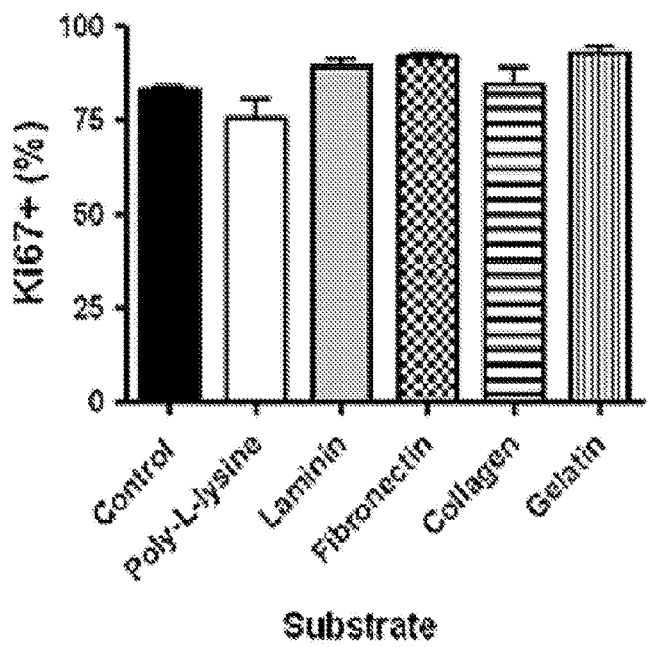
Figure 2A:
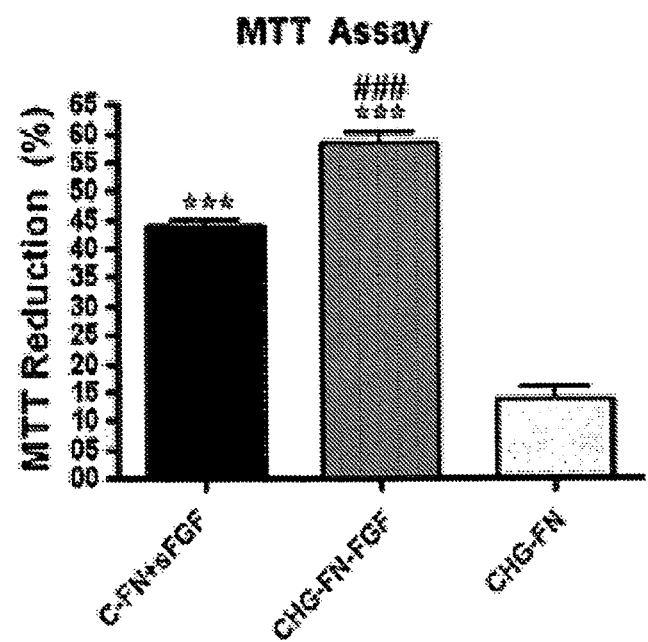
FIG. 2: Effect of immobilized FGF-2 on proliferation and survival of NSCs. Secondary NSCs grown as neurospheres in DMEM/F12 supplemented with B27+/−10 ng/ml FGF-2 for 2 days. After dissociation, cells were grown on chitosan-fibronectin coated 96 well plates with or without heparin (0.5 mg/mL)—genipin (0.45 mM) and FGF-2 (1000 ng/ml). Control only received FGF-2 daily. (A) MTT Assay (B) C-Fn-FGF-2 (soluble) control (C) C-H-G-Fn-FGF-2 (bound) (D) CHG-Fn−. C-Fn: Chitosan-fibronectin. CHG-Fn+: Chitosan-heparin-genipin-fibronectin+bound FGF-2. CHG-Fn−: Chitosan-heparin-genipin-fibronectin, no FGF-2. Scale bar: 100 μm.
Figure 2B:
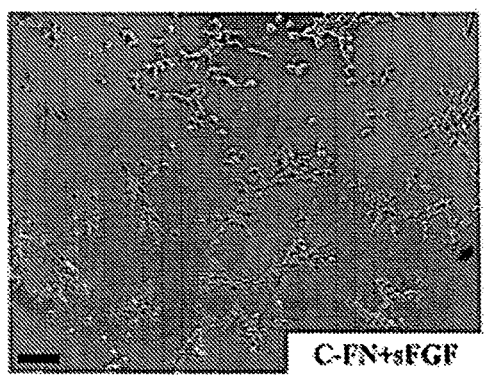
Figure 2C:
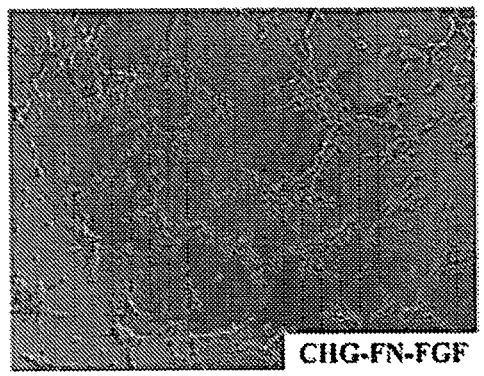
Figure 2D:
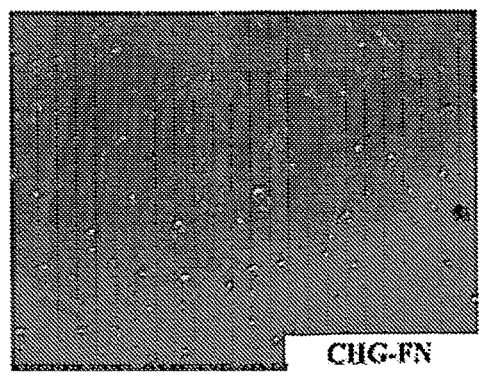

A novel multi-functional growth matrix is disclosed that can be used as a biomaterial scaffold for mammalian tissue regeneration and repair. In one embodiment, the growth matrix is a 2-dimensional multi-functional scaffold that supports the expansion of stem cells. For example, the 2-dimensional multi-functional scaffold can be used to grow human embryonic stem cells (hESCs) and induced pluripotential stem cells (iPSCs). In another embodiment, the growth matrix is a 3-dimensional multi-functional scaffold that supports the expansion of stem cells. For example, such 3-D scaffolds can be used as a vehicle for transplanting stem cells. The multi-functional matrix disclosed herein promotes both the proliferation and pluripotency of stem cells by attaching a growth-promoting protein to a surface of a culture plate, thereby stabilizing the growth-promoting protein. The matrix can also be further modified by attaching an adhesive component, such as an extracellular matrix protein. Such a biomaterial scaffold promotes tissue regeneration from primitive cells.

In one exemplary embodiment, the disclosed matrix is highly suitable for propagating neural stem cells in vitro. In contrast to systems/approaches available in prior art, the disclosed matrix promotes both the proliferation and pluripotency of stem cells at a reduced frequency of cell feedings (no need for daily feedings) while the proportion of proliferating and undifferentiated cells is significantly greater than cells propagated under standard growth conditions. The terms "matrix" and "scaffold" are used herein interchangeably and refer to a structure capable of supporting 2D and/or 3D cell growth.

Stem cells that can be supported by the disclosed growth matrix include, but not limited to, embryonic stem cells, pluripotential stem cells, somatic stem cells, adipose-derived stem cells, mesenchymal stem cells, hematopoietic stem cells or umbilical cord blood stem cells, oligodendrocyte progenitors, or FGF responsive progenitors that will grow on an adherent substrate, in the presence or absence of other growth-promoting proteins. In a preferred embodiment, the stem cells are mammalian and more preferably limited to rodent, primate or human. In another embodiment, the stem cells that can be supported by the disclosed growth matrix also include the induced pluripotential stem cells (iPSCs) or the stem cells derived from iPSCs.

In another embodiment, the 3-D scaffold is used as a vehicle for transplanting stem cells on a supportive matrix. In a further embodiment, stem cells are attached to a scaffold and are transplanted into the lesions created by a spinal cord, traumatic brain injury or a stroke to reconstruct critical neural circuits. In one embodiment, stem cells are attached to a scaffold and are transplanted into non-neural tissues. In a further embodiment, the stem cells are mesenchymal stem cells. In another embodiment, the non-neural tissue is bone, cartilage, liver, pancreas, heart, skin, bladder, skeletal muscle, lung or kidney.

The backbone of the disclosed matrix or scaffold is made from chitosan, which is derived by alkaline deacetylation of chitin. This chitosan backbone yields repeating units of glucosamine and N-acetylglycosamine. Chitosan is a natural polysaccharide similar in structure to glycosaminoglycans which allows for easy modification.

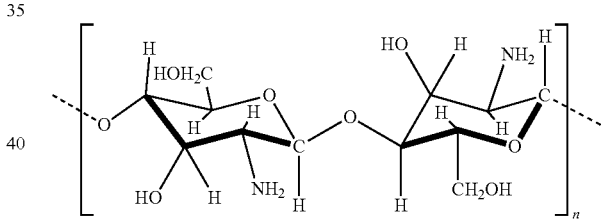

It is second in abundance to cellulose making it a cost effective material. Chitosan dissolves easily in a weak acid solution such as acetic acid. Once dissolved as a viscous liquid, chitosan can be used to coat the surfaces of cell culture dishes or used to form complex 2D/3D scaffolds. CNS injuries are not uniform in shape or size; therefore a scaffold that is injectable and will mold to the injured tissue is necessary. The chemical structure of chitosan easily allows for modification of its chemical structure, thus making it a very attractive and versatile material.

The disclosed matrix having chitosan backbone therein is further modified to immobilize a growth-promoting protein in a biological and stable form by covalently linking a growth-promoting protein binding partner to the chitosan using genipin, a naturally occurring and biologically safe cross-linking agent. Specifically, the disclosed matrix is made from (i) chitosan, (ii) genipin, (iii) growth-promoting protein binding partner, and (iv) growth-promoting protein. Preferably, the disclosed matrix further contains (v) an adhesive component. In one embodiment, the matrix comprises (i) chitosan, (ii) growth-promoting protein binding partner, (iii) genipin, (iv) growth-promoting protein, and (v) adhesive component. In the preferred embodiment, the method also has one or more washing/rinsing steps between the additions of one or more components. In a preferred embodiment, the matrix comprises a scaffold with fibronectin, immobilized FGF-2, heparin, genipin and chitosan. In a more preferred embodiment, the matrix comprises a scaffold of chitosan, linked heparin to chitosan via genipin, and immobilized thereon FGF-2 and fibronectin. Without being bound by theory, in one embodiment, the FGF-2 and fibronectin are immobilized on heparin by forming one or more non-covenant bridges, such as electrostatic, van der Waals, and hydrophobic.

Although, the crosslinking agent used in the disclosed matrix is preferably genipin, the matrix can also be prepared with glutaraldehyde, formaldehyde, tripolyphosphate (TPP), 1-ethyl-3-(3-dimethylaminopropyl) carbodiimide (EDC), β-glycerophosphate (βGP), calcium phosphate, citrate, sulfate, Fe(III), Ho-166, poly ethylene glycol dialdehyde diethyl acetal (PEGDDA), oxalic acid, glyoxal, N,N'-Methylene bisacrylamide without departing from the spirit of the invention.

The growth-promoting protein binding partner is selected from heparin, heparan sulfate or a heparan sulfate analogue (see e.g., Guimond, S. E., et al. *Int J Exp Pathol.* 2004 August; 85(4): A62-A63; incorporated herein by reference in its entirety). Preferably, the growth-promoting protein binding partner is heparin.

The growth-promoting protein is not particularly limited as long as it can promote growth of the stem cells applied therein. The growth-promoting protein is selected from an Activin, an Adrenomedullin (AM), an Angiopoietin (Ang), an Autocrine motility factor (AMF), a Cadherin, a Ciliary neurotrophic factor (CNTF), an Epiregulin, an Erythropoietin (EPO), a Follistatin, a fibroblast growth factor (FGF), platelet-derived growth factor (PDGF), epidermal growth factor (EGF), heparin binding epidermal growth factor (HB-EGF), a Glial cell line-derived neurotrophic factor (GDNF), a Granulocyte colony-stimulating factor (G-CSF), a Granulocyte macrophage colony-stimulating factor (GM-CSF), a Growth differentiation factor (GDF), a Hepatoma-derived growth factor (HDGF), an Interleukin, an Insulin-like growth factor I or II (IGF), a Leukemia Inhibitory Factor (LIF), a Migration-stimulating factor (MSF), a Myostatin (GDF-8), a Nerve growth factor (NGF), a Neurotrophin (NT-3, 4/5, 6), a Netrin, a Notch Receptor Ligand, a Noggin, an Oncostatin, a SLIT, a Stem Cell Factor (SCF), a Sonic hedge hog (SHH), a Neurite growth promoting factor (NEGF), a Placental growth factor (PlGF), a Thrombopoietin (TPO), a Transforming growth factor alpha (TGF-α), a Transforming growth factor beta (TGF-β), a Tumor necrosis factor alpha (TNF-α), or a WNT. In a preferred embodiment, the growth-promoting proteins can readily form non-covalent interactions with heparin include, but not limited to, Brain-derived neurotrophic factor (BDNF), Bone morphogenetic protein (BMP), Epidermal growth factor (EGF), one of the Fibroblast growth factors (FGF-2, 4, 7, 8, 10, 18), Heparin Binding Epidermal Growth Factor (HbEGF), Hepatocyte growth factor (HGF), Keratinocyte growth factor (KGF), Neuregulin (NRG), Neurite growth promoting factor (NEGF 1/2), Platelet-derived growth factor (PDGF) or Vascular endothelial growth factor (VEGF). In a preferred embodiment, the growth-promoting protein is selected from fibroblast growth factor (FGF), platelet-derived growth factor (PDGF), epidermal growth factor (EGF) or heparin binding epidermal growth factor (HB-EGF). In a more preferred embodiment, the growth-promoting protein is fibroblast growth factor (FGF), and even more preferably, FGF-2.

The adhesive component is an extracellular matrix protein, an extracellular matrix peptide, an adhesive saccharide, or combinations thereof. The extracellular matrix protein is selected from Fibronectin, Laminin, Vitronectin, Fibrillin, Fibrinogen, Plasminogen, Plasmin, Aggrecan, Brevican, Tenascin, Collagen, Elastin, Hyaluronic acid proteoglycan, Keratan sulfate proteoglycan, Heparan sulfate proteoglycan, Chondroitin sulfate proteoglycan, Syndecan-1 (proteoglycan), IGF Binding Protein or combinations thereof. The adhesive saccharide is preferably cellulose. The extracellular matrix peptide is a peptide selected from poly-DL-lysine, such as PDL or PLL, poly-DL-ornithine, a short peptide sequence RGD (Arg-Gly-Asp), or a short peptide sequence IKVAV (Ile-Lys-Val-Ala-Val, SEQ ID NO: 1). In a preferred embodiment, the extracellular matrix peptide is RGD or IKVAV (SEQ ID NO: 1). Those of skill in the art would also understand that such peptides can be extended/modified without departing from the spirit and scope of the invention. For example, RGD also includes sequences RGD-S (SEQ ID NO: 2), G-RGD-S (SEQ ID NO: 3), G-RGD-SP (SEQ ID NO: 4), G-RGD-TP (SEQ ID NO: 5), N-MeGly-RGD-SP (SEQ ID NO: 6), G-RGD-SPK (SEQ ID NO: 7), RGD-SPASSKP (SEQ ID NO: 8), and ACDC-RGD-CFCG (SEQ ID NO: 9). For example, IKVAV (SEQ ID NO: 1) also includes sequences CSRARKQAAS-IKVAV-SADR (SEQ ID NO: 10) (also trifluoroacetate) and S-IKVAV (SEQ ID NO: 11).

As researchers move from the bench to the clinic, there is a real need for a xenogeneic-free culture system. Ideally, stem cell derivation, establishment, cell banking and undifferentiated expansion should all be done using xenogeneic free components (i.e., not derived from living tissue). By using peptide sequences of extracellular matrix peptides, such as RGD and IKVAV (SEQ ID NO: 1), those skilled in the art can avoid costs and potential contamination associated with using extracellular matrix components extracted from tissue or cultured cells.

In designing the disclosed multifunctional matrix, the goal was to enable the growth-promoting protein to be slowly released into the medium to stimulate growth. However, in evaluating the matrix of present invention, it was surprising to find that very little of the growth-promoting protein was released. Furthermore, stem cells plated onto the multi-functional matrix, remained in a multipotent, proliferating state for at least 3 days without renewing the growth-promoting protein. The cells grown on the matrix also remained less mature and more highly proliferative than cells maintained on a similar scaffold that lacked the tethered growth-promoting protein. Moreover, the growth-promoting protein can remain biologically active while bound within the disclosed matrix for about 7 days. In contrast, the matrices of prior art do not have stably immobilized, growth-promoting proteins of defined identify and are, thus, not suitable for therapeutic use. Therefore a major advantage of the matrix herein is that it can be formulated using defined components, that it will stabilize the biological activity of those components and that it can maintain stem cells in a more uniform, proliferating and primitive state. It is also well known to those knowledgeable in the art that stem cell propagation using presently available methods require that the cells be fed on a daily basis, whereas the disclosed matrix reduces the time-consuming and tedious task of feeding the cells on a daily basis, while maintaining their stemness.

The disclosed matrix can be prepared by (i) coating the bottom of a chamber with a chitosan solution; (ii) drying the chitosan solution to form a chitosan layer; (iii) neutralizing the acidity of the chitosan layer by applying a basic aqueous solution (typically sodium hydroxide or ammonium hydroxide) with rinses to remove the basic aqueous solution (iv) binding a growth-promoting protein binding partner to the chitosan layer; (v) cross-linking the growth-promoting protein binding partner to the chitosan layer using genipin; (vi) applying a solution of a growth-promoting protein; (vii) allowing the growth-promoting protein to adhere, (viii) applying a solution of an adhesive component; and (ix) allowing the adhesive component to adhere, which creates a multifunctional film. To support the expansion of stem cells, the method further has a step of (x) seeding the population of stem cells onto the chamber and culturing the stem cells. Although, the method of preparing the disclosed multifunctional matrix is provided in a sequence of steps, it will be apparent to those skilled in the art that the sequence can be modified and yet arrive at the disclosed multi-functional matrix.

Stem cells plated onto the disclosed matrix remain in a multipotent and proliferative state without a need of providing soluble growth-promoting proteins. Moreover, they remain less mature and more highly proliferative than cells maintained on a fibronectin-coated substrate in a culture medium supplemented with soluble growth-promoting proteins (e.g., soluble FGF-2). In a preferred embodiment, the growth-promoting protein binding partner is heparin and the growth-promoting protein is one or more growth factors, such as fibroblast growth factor-2 (FGF-2). In a more preferred embodiment, the matrix is made from a scaffold of chitosan, genipin-linked heparin with immobilized FGF-2 and fibronectin.

The disclosed method can produce a scaffold that is highly suitable as a vehicle for cell transplantation to repair tissue damage, such as CNS injury. In one embodiment, the present invention provides a method to grow stem cells in culture which may then be used to repair injured mammalian tissue. In another embodiment, the present invention provides a method to repair an injured tissue by delivering the stem cells upon a scaffold composition into a subject. The scaffold composition is made from chitosan, a genipin immobilized growth-promoting factor binding partner, a growth-promoting protein, and an adhesive component. In a preferred embodiment, the scaffold composition is comprised of chitosan, genipin-linked heparin with immobilized FGF-2 and fibronectin.

In one embodiment, a method to manufacture an injectable multifunctional microsphere scaffold is provided to achieve a scaffold that is highly suitable as a vehicle for cell transplantation to repair brain injuries. In an exemplary embodiment, to serve as a vehicle for cell transplantation, a chitosan solution is electrosprayed into a coagulation bath to generate microspheres (range: 30-100 µm) that can be subsequently modified. Neural stem cells seeded onto the multifunctional microspheres can be propagated in culture, and the microspheres containing the cells are small enough to be injected using a 26 gauge Hamilton syringe into the brain that had previously sustained cortical contusion injuries. Thus, this multifunctional scaffold can be used as a cellular and growth factor delivery vehicle to promote the regeneration of nervous tissue injury after brain injuries.

Figure 8:
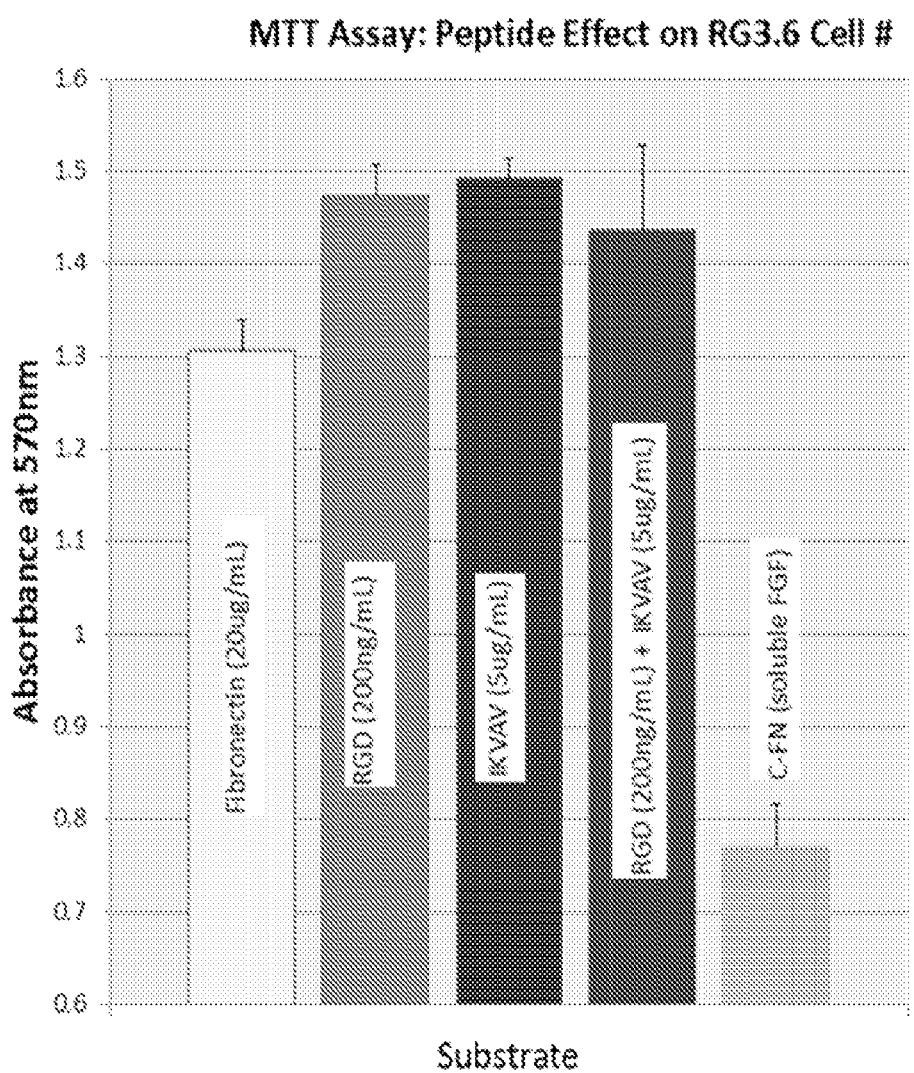
FIG. 8: Effect of immobilized peptides on proliferation and survival of neural stem cells. Culture plates were coated with chitosan. The plates were then further modified. Some wells were further coated with heparin-genipin and then incubated with FGF-2 (1 µg/ml) and then adsorbed with adhesion peptides. Wells used as controls received soluble FGF-2 daily on chitosan-fibronectin conditions only. The wells were then seeded with the RG3.6 neural stem cell line and grown for three days. MTT assay was used to measure cell growth between conditions: Fibronectin (yellow), RGD (blue), IKVAV (red), RGD+IKVAV (purple), and control (C-FN, green). All peptides were incubated at equal molarity (45.45 nM). RGD: arginine-glycine-aspartic acid; IKVAV—isoleucine-leucine-valine-alanine-valine.

In one embodiment, the microspheres are modified by the addition of fibronectin. Fibronectin not only aids in the adherence of the cells to chitosan, but may also enhance their proliferation as shown in FIGS. 1 and 2 and maintain their stemness as shown in FIG. 3, due to the molecular structure of fibronectin. Arginine-glycine-aspartic acid (RGD), first identified in fibronectin, is contained within other ECM proteins such as collagen, vitronectin, thrombospondin, von Willebrand factor, fibrinogen, gelatin and some laminins. Consistent with a role for the RGD peptide in enhancing the proliferation of the neural stem cells, RG3.6 cells grown on fibronectin coated substrates exhibit a higher mitotic index (see. FIG. 1). Collagen also possesses an RGD sequence, but the cells do not proliferate as significantly when attached to collagen. This may be due to collagen's negative charge and the resulting gel-like coating formed when bound to chitosan. Importantly the RGD sequence binds to the $\alpha 5\beta 1$ integrin receptor whose intracellular amino terminus influences cellular migration, proliferation, self-renewal and differentiation. It has been observed that reducing $\alpha 5\beta 1$ expression in cortical progenitors increased their differentiation. A similar effect of specific proteins on $\alpha 6\beta 1$ was observed. This receptor is activated by netrin-4 and laminin-$\gamma 1$. A reduction in these proteins increases the differentiation of NSC. This concept was applied to an in vivo application using a hyaluronic acid based hydrogel with immobilized RGD for brain tissue engineering. Transplantations after cortical damage using hyaluronic acid-RGD scaffolds enhanced cell infiltration and angiogenesis into the matrix, while simultaneously inhibiting glial scar formation. An increase in neurite extension was also observed. As shown in FIG. 8, the fibronectin may be substituted with the RGD peptide with comparable performance.

The modified chitosan microspheres disclosed herein can be designed to allow FGF-2 to be tethered to the surface of the scaffold, which differs from systems of prior art that have used the spheres as a method for either encapsulating growth factors or transplantable cells. FGF-2 is a known survival factor for neural precursors and maintains these cells in a primitive state. FGF-2 has been shown to increase the numbers of stem/progenitor cells in the subventricular zone following TBI.

By immobilizing the FGF-2 to the surface of the chitosan, it is presented to the cells in a more biologically active form (due to heparin binding) and is more available to adherent cells when bound rather than in soluble form either supplied through media or released from encapsulation. The inventors have discovered that cells maintained on the multifunctional film (matrix) do not need to be fed for at least 3 days after plating, and yet the proportion of proliferating and undifferentiated cells is significantly greater than cells propagated under standard growth conditions. Stem cells normally require feeding on a daily basis; however, with the disclosed matrix, the cells can clearly be left untended for at least 3 days.

It will be appreciated by persons skilled in the art that the present invention is not limited to what has been particularly shown and described herein above. Rather, the scope of the present invention is defined by the claims that follow. It should further be understood that the above description is only representative of illustrative examples of embodiments. For the reader's convenience, the above description has focused on a representative sample of possible embodiments, a sample that teaches the principles of the present invention. Other embodiments may result from a different combination of portions of different embodiments.

EXAMPLES

Example 1 (Stem Cell Morphology, Proliferation and Differentiation)

Neural Stem Cells: Two cell types were used to evaluate the functionality of the modified chitosan films and microspheres: an immortalized cell line, RG3.6, that was created from embryonic day 13.5 green fluorescent protein positive (GFP+) rat neocortical cells; and primary NSCs harvested from embryonic day 13.5 EGFP (SD-Tg(GFP)Bal/2Rrrc (RRRC:0065) rat neocortex. The RG3.6 cell line was used instead of primary cells for specific experiments to eliminate several variables seen with heterogenous primary cell cultures and to achieve greater consistency during substrate optimization. Both RG3.6 and primary NSCs were maintained in DMEM/F12 media supplemented with B27, gentamycin (50 µg/ml), apo-transferrin (50 µg/ml) and rhFGF-2 (10 ng/ml+1 ng/ml Heparan Sulfate). They were either grown as neurospheres or as an attached monolayer on polyornithine/fibronectin coated petri dishes.

Chitosan Films: A 3% w/v low molecular weight chitosan solution was prepared in 2% acetic acid v/v. Chitosan (low molecular weight ~50 kDa) was purchased from Sigma (St Louis, Mo.). The solution was pipetted into two-well glass chamber slides (NUNC, Rochester, N.Y.) to coat the bottom of chamber. The remaining solution was removed and the slides were set to dry for 2-3 h at room temperature. Chitosan coatings were neutralized in 0.5 M NaOH (Sigma; St Louis, Mo.) for 10 minutes and then rinsed 3 times in sterile deionized water for 5 minutes each. The chitosan was subsequently adsorbed with solutions of fibronectin (10 µg/mL), laminin (20 µg/mL), gelatin (0.1%), collagen type I (0.1 mg/mL), or poly(L-lysine) (0.05 mg/mL) prepared in $dH_2O$.

Stem Cell Morphology, Proliferation and Differentiation: To establish which surface modifiers best maintained the morphology of NSCs, the RG3.6 cell line was seeded onto chitosan adsorbed with fibronectin, laminin, gelatin, type I collagen, or poly(L-lysine) and compared to RG3.6 cells grown on chitosan without adsorbed matrix factors or polymer. After 4 days of growth the cells were fixed and stained for actin and counterstained using DAPI. NSCs are morphologically distinct, with a few long processes. RG3.6 cells responded differently when grown on chitosan substrates with varying adhesive proteins. Substrates coated with fibronectin promoted the NSC morphology (see FIGS. 1A, 1B, and 1C). RG3.6 cells maintained on fibronectin had 1-3 processes that were quite long and straight (49±5 µm) and they lacked branches. RG3.6 cells grown on laminin also possessed processes that were few in number and long (35±3 µm), but they were shorter than the processes of the cells grown on fibronectin. Cells grown on type I collagen (11±1 µm), gelatin (31±2 µm) and unmodified chitosan (13±1 µm) had short processes. Cells grown on poly(L-lysine) had numerous, short processes (17±1 µm) that branched frequently.

Stem Cell Proliferation: RG3.6 cells were stained for Ki67, which is a marker of cells undergoing mitosis. These studies showed that the mitotic indexes of RG3.6 cells grown on all substrate conditions were high and differed only slightly, but two ECM proteins fibronectin and gelatin resulted in the highest mitotic index at 92±1% and 93±2%, respectively (see FIG. 1D). The mitotic indices of cells grown on the other substrates were: laminin, 89±2%; collagen, 87±4%; poly(L-lysine), 77±5%; and unmodified chitosan, 82±1%.

In summary, chitosan was non-toxic to NSCs (data not shown) but the cells required adhesive peptides to grow efficiently on the scaffold. Proliferative rates were high on all chitosan substrates, however they were noticeably higher when the chitosan was coated with fibronectin or gelatin.

Example 2 (Scaffold Efficiency)

The biological, activity of the human fibroblast growth factor-2 (hFGF-2) bound to the scaffold was verified by measuring cell growth using the MTT assay and analyzing the morphology of NSCs. Heparin sodium salt from bovine intestinal mucosa was purchased from Sigma (St Louis, Mo.). Recombinant human-fibroblast growth factor-2 (rh-FGF-2) was purchased from Peprotech (Rocky Hill, N.J.). Genipin was purchased from Wako Pure Chemical Industries, Ltd. (Osaka, Japan).

Cell growth: Ninety six well plates were coated with 50 µl of 3% chitosan and air-dried overnight. Select coated wells were incubated with heparin (0.5 mg/mL) and genipin (0.45 mM) overnight at room temperature. The heparin-genipin solution was prepared in 50 mM HEPES+0.9% NaCl solution (HBS) (VWR; West Chester, Pa.). Other wells were incubated in HBS only overnight. The following day, fibronectin (10 ug/mL) was added to each well for 4 hours at 37° C. to enhance cell attachment to the chitosan and modified chitosan substrates. Subsequently 1 µg/mL FGF-2 was added to half the chitosan-heparin-genipin wells. Other wells were untreated. NSCs were plated into each condition at high ($5 \times 10^4$ cells/well) and low ($2 \times 10^4$ cells/well) densities. Cells in the chitosan-fibronectin condition received FGF-2 in the media daily as these cells would normally when propagating in vitro. Cells on the multifunctional scaffold did not receive medium supplemented with FGF-2. The former condition served as a control. Cultures were grown for three days before being analyzed for cell growth using the MTT Assay.

Morphological analyses: NSCs are a morphologically distinct cell type with typically, 2 very long processes. Cell process lengths were measured using Sigma Scan Pro software (Systat Software, San Jose, Calif.). The average number of processes extending from each cell was manually calculated. Statistical analyses were performed using an ANOVA with Tukey post-hoc. Data are expressed as the mean±standard error of mean (SEM).

MTT reduction assay: MTT assay is a colorimetric assay that measures the reduction of a yellow substrate 3-[4,5-dimetylthiazol-2-yl]-2,5-diphenilttetrazolium (MTT, purchased from Sigma, St Louis, Mo.) in the cell into an insoluble purple formazan product. Briefly, 10 µl of a 5 mg/ml MTT solution in PBS was added to 100 µL of medium and incubated for 2-4 h in the cell incubator at 37° C. The reaction was stopped by adding 100 µl of a solution containing 50% (w/v) N,Ndimethylformamide and 20% SDS (pH 4.8). The plates were maintained overnight in the incubator at 37° C. and the absorption at 560-690 nm was determined using a microtiter plate reader (PowerWave 200, Bio-tek Instruments).

Cell Differentiation Assays: To generate differentiated cells, NSCs were seeded onto poly-d-lysine and laminin coated dishes and maintained for 24 h in medium, then the FGF-2 was removed from the medium whereupon the cells differentiated over the following four days. To evaluate proliferating cells using standard culture conditions, NSCs were seeded in medium onto chitosan-coated dishes with adsorbed fibronectin (10 µg/mL). Ten percent of the medium was changed every day and replaced with equal volume of 10× FGF-2 containing media (100 ng/mL). To evaluate the growth and differentiation of the NSCs when seeded onto the multifunctional scaffold, NSCs were seeded onto chitosan-coated dishes with covalently bound heparin and adsorbed fibronectin. One 1 µg/mL FGF-2 (in 1 mg/mL BSA solution) was added to the dish and incubated for 3 hours at room temperature. The FGF-2 solution was then aspirated and rinsed gently, twice to remove any unbound growth factor. NSCs were seeded onto the plates and maintained for 4 days in the basal growth medium (which lacked soluble FGF-2).

Cells were scraped from the plates in lysis buffer and stored until Western Blot protein analyses. Protein concentrations were determined using the BCA assay (ThermoScientific, Rockford, Ill.). Western blots were analyzed for the stem cell and progenitor markers brain lipid binding protein (BLBP) using a rabbit anti-BLBP antiserum at 1:1000 (Abeam, Cambridge Mass.); sex determining region Y-box 2 (Sox2) using rabbit anti-Sox2 antisera 1:200 (Chemicon, Temecula, Calif.); beta tubulin (TUJ1) 1:1000 (Covance, Princeton, N.J.), microtubule associated protein-2 (MAP2) using a rabbit anti-MAP2 1:200 (Sigma).

Stem Cell Morphology and Growth: RG3.6 cells and primary NSCs responded differently when grown on the more highly modified chitosan substrate. The cells preferred the addition of genipin cross-linked heparin, fibronectin and immobilized FGF-2 to the chitosan substrate. When grown on this complex, the MTT assay returned a 2.5 fold higher value than NSCs grown on the same complex without immobilized FGF-2 (see FIG. 2A). The higher number of cells growing on the scaffold condition with immobilized FGF than on the chitosan-fibronectin condition, which, received FGF-2 in the media, daily was also evident microscopically (see FIG. 2B-2D). To our surprise, the immobilized FGF-2 was superior in promoting NSC cell proliferation compared to the standard growth conditions used to propagate NSCs. NSCs cells are typically grown in culture as a monolayer, receiving soluble FGF in media changes daily.

To establish whether the scaffold also would enhance the growth of non-immortalized NSCs, primary NSCs were grown on fibronectin or on a multifunctional film comprised of chitosan, genipin-linked heparin, FGF-2 and fibronectin. This multifunctional film promoted both the proliferation and pluripotency of NSCs while reducing the frequency of feeding the cells (see FIG. 3A-3B). As a measure of their NSC phenotype the level of brain lipid binding protein (BLBP) was evaluated (see FIG. 3C-3D) by Western blot. As an index of their proliferative state the protein levels of proliferating cell nuclear antigen (PCNA) were measured. The expression of class III beta tubulin (TUJ1) and microtubule associated protein-2 (MAP-2) was measured to evaluate whether the cells differentiated towards neurons, and whether the cells had differentiated towards astrocytes by measuring levels of glial fibrillary acidic protein (GFAP) or whether the cells had remained as stem cells or progenitors by measuring the levels of SRY box-2 binding protein (SOX2). These studies showed that primary NSCs grown on the multifunctional scaffold had higher levels of PCNA, BLBP and SOX-2 compared to NSCs maintained under standard growth conditions. Furthermore, GFAP was undetectable and expression of TUJ1 was significantly lower when grown on the multifunctional scaffold than when maintained under standard growth conditions. These data support the conclusion that the multifunctional scaffold maintains the NSCs in a proliferative, stem cell state. In particular these studies indicate that the immobilized FGF-2 was superior to soluble FGF-2 in maintaining their stemness, limiting their differentiation and even delaying the formation of astrocytes.

Example 3 (3-Dimension Scaffold Characterization)

Preparation of Chitosan Microspheres: Chitosan powder (1.5 g) was dispersed in 50 ml of water containing 2.0% v/v acetic acid to create a 3% chitosan solution. The chitosan solution was mechanically stirred at 700 rpm until completely dissolved. The resulting solution was collected and centrifuged at 2,000 rpm for 10 minutes. Subsequently, the supernatant was collected and the remaining impurities that pelleted were discarded. Chitosan microspheres were formed by extruding the acid chitosan solution through a syringe at a flow rate of 5 ml/hr into a basic coagulation bath, consisting of 2.5 M sodium hydroxide: methanol: water (20:30:50 v/v). To reduce the surface tension on the end of the needle and thus reduce the size of the microspheres to a desired range, a 25 kV electric current was applied. Next, the spheres were filtered through a 100 μm strainer to remove any oversized spheres. They were removed from the ionic solution and rinsed four times in distilled water to eliminate any residual sodium hydroxide and methanol. They were then sterilized in 70% ethanol for 30 minutes. Microsphere size was measured using Sigma Scan Pro 5 software. Frequency distribution of microsphere diameter was also quantified. Following rinses in distilled water, microspheres were coated overnight with heparin (0.5 mg/ml) and genipin (0.45 mM) in HBS to cross-link the heparin to the microspheres, as described previously. The following day the heparin cross-linked spheres were rinsed 3 times 10 minutes in HBS and incubated for 4 hours with fibronectin (10 μg/mL) and 2 h in 1 μg/ml, rhbFGF.

Figure 4A:
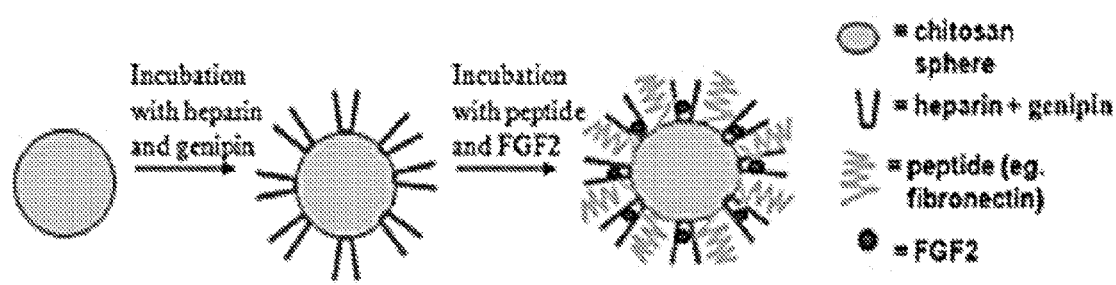
FIG. 4: Characterization of transplantable modified microspheres. Microspheres formed by ionic coagulation and electrospraying were compared in size to spheres formed by a coaxial airflow or no air. (A) Schematic of microsphere preparation. (B) 20× phase contrast images of electrosprayed chitosan microsphere. (C) Size distribution of electrosprayed microspheres. (D) Frequency distribution of chitosan microsphere diameter. (E) Toluidine blue staining of heparin covalently cross-linked to chitosan microspheres. (F) NSCs grown on electrosprayed microspheres modified with heparin-genipin-FGF-2 and adsorbed with fibronectin.
Figure 4B:
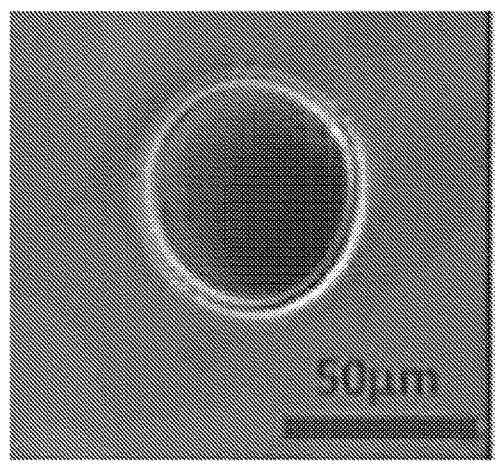
Figure 4C:
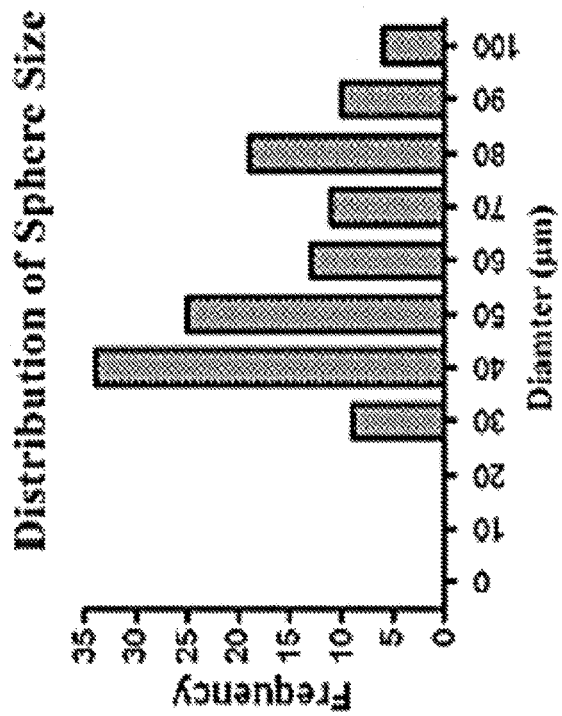
Figure 4D:
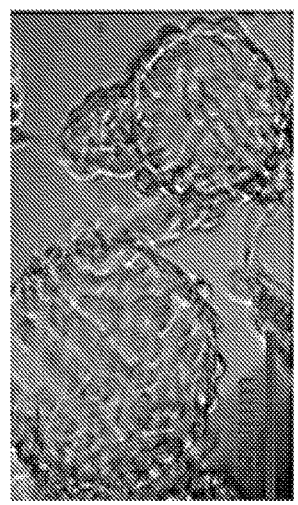
Figure 4E:
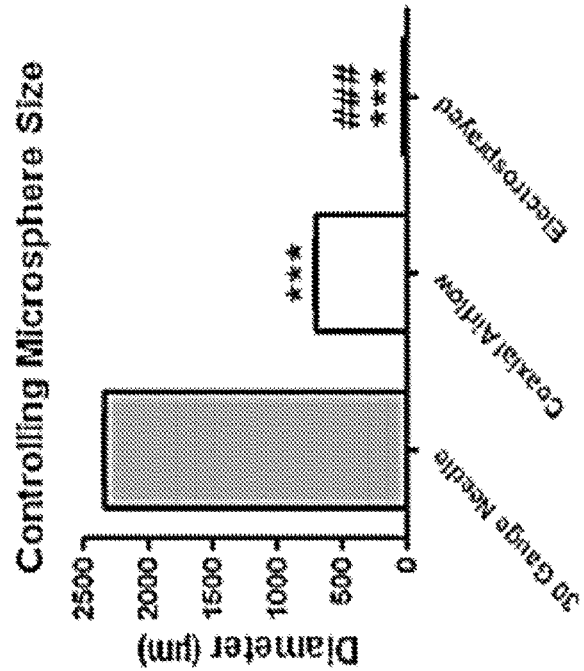
Figure 4F:
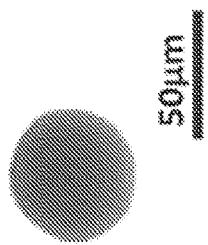

This example illustrates a manufacture of a vehicle to facilitate the delivery of neural precursors into brain injuries with the cells adhered to the surface of the microspheres. A schematic for the vehicle design is presented in FIG. 4A. Previously generated microspheres using a coaxial airflow ranged in size from 200-500 μM in diameter. Such spheres are too large for injections using 23 gauge needles. The optimal sphere size for transplantation through a 23 gauge Hamilton syringe is between 20-100 μm. To overcome the shortcomings of prior art, it was found that the size of the microspheres can be decreased by using an electric current. The high flow rate and high voltage reduced the surface tension on the syringe allowing for smaller droplets to be "sprayed" into the coagulation solution. Microspheres between 10-100 μm were formed using 22 kV and a flow rate of 90 ml/h with, on average 64 μm in diameter (see FIGS. 4C and 4D). The majority of the spheres fell within the 30-100 μm range as seen in the frequency distribution. The microspheres were modified by covalently cross-linking heparin to chitosan through genipin to allow the immobilization of FGF-2. Fibronectin was also added for cell adhesion. Toluidine blue stain for heparin was evident on the microspheres (see FIG. 4E). To establish whether NSCs would adhere and grow on these microspheres, a single cell suspension of RG3.6 cells was mixed with microspheres and incubated overnight, whereupon they attached to the spheres (see FIG. 4F). These 3-D cultures were maintained for 10 days in vitro with daily media changes. RG3.6 proliferated well on the scaffold, with limited cell death.

Example 4 (Transplantation Studies)

Controlled Cortical Impact: Two month old adult Sprague Dawley male rats were anesthetized using a ketamine/xylazine mixture (90 mg/kg and 10 mg/kg) delivered by intraperitoneal injection. The fur covering the head was removed using an electric razor and a midline incision made through the scalp using a scalpel. The skin was deflected and a craniectomy made using a 5 mm diameter trephine. The trephine was placed midway between Bregma and Lambda, with the edge of the trephine adjacent to midline. Cold PBS was suffused onto the surface of the skull during the craniotomy to reduce the generation of heat that could cause damage to the underlying dura mater and neocortex. The skull flap was removed and the animal placed into a stereotactic apparatus under the controlled cortical impactor (CCI) (eCCI 6.3 device built by Custom Design and Fabrication, Richmond, Va.). The tip of a 3.5 mm diameter anvil was zeroed by bringing it into contact with the exposed dura mater. The velocity of the impactor was set at 4.0±0.2 m/s, the depth of penetration to 1.5 mm and the duration of deformation to 150 msec. After impact, the integrity of the dura mater was confirmed and the scalp incision sutured with 3-0 nylon thread. Buprenorphine (0.05 mg/kg, SC) was administered post-operatively and the rats were placed on heating pads maintained at 37° and monitored continuously for 2 h after surgery. In addition, immediately after surgery, all subjects received 3% body weight of 0.9% saline subcutaneously (SC) to prevent dehydration.

Transplantation: Subacute transplantations were performed 7 days after CCI injury. The animals were anesthetized again using a ketamine/xylazine mixture and the sutures were removed to expose the skull. Cell-sphere complexes were collected from culture dishes and resuspeuded in phenol-free media without supplements. A 26 gauge Hamilton syringe was used to inject the scaffold at three different depths: 1.5, 1.0 and 0.5 mm below the dura mater. One μL was injected at each depth over 5 minutes, with 5 minute intervals between each injection and 10 minutes following the final injection. The scalp incision was sutured with 3-0 nylon thread and the animals placed onto a 37° C. heating pad until they were fully awake. All of the procedures performed on aminals in this report were approved by the New Jersey Medical School IACUC under animal protocol ##08056.

Immunofluorescence: For in vitro studies, cells were fixed in 3% paraformaldehyde and stained for F-actin with phalloidin conjugated rhodamine, at 0.1 mg/ml (Sigma, St. Louis Mo.), for the proliferation marker Ki-67 (Vector Laboratories, Burlingame Calif. 1:1000) and counterstained using 4',6'-diamidino-2-phenylindole (DAPI, Sigma, 1 μg/ml). For in vivo studies, rats were perfused 3 days post transplantation using 4% paraformaldehyde (PFA). The brains were collected and kept in 4% PFA ON. The next day the brains were rinsed with PBS and cryoprotected by immersion in 30% sucrose in dH2O. After one change of sucrose solution, the brains were placed into plastic cryomolds and frozen in OCT on a dry-ice-ethanol slush. The brains were cryosectioned at 40 and 15 μm thickness and stained using mouse anti-Nestin antibody (Developmental Studies Hybridoma Bank, Iowa, 1:5). Sections were incubated in secondary antibodies for 2 h at room temperature (all from Jackson Immunoresearch, West Grove, Pa.; 1:200). All secondary antibody combinations were carefully examined to ensure that there was no cross-talk between fluorescent dyes or cross-reactivity between secondary antibodies. No signal above background was obtained when the primary antibodies were replaced with pre-immune sera. After secondary antibody incubation the sections were washed, counterstained with DAPI for 5-10 minutes, and coverslipped with GelMount (Biomeda, Foster City, Calif.).

Figure 5A:
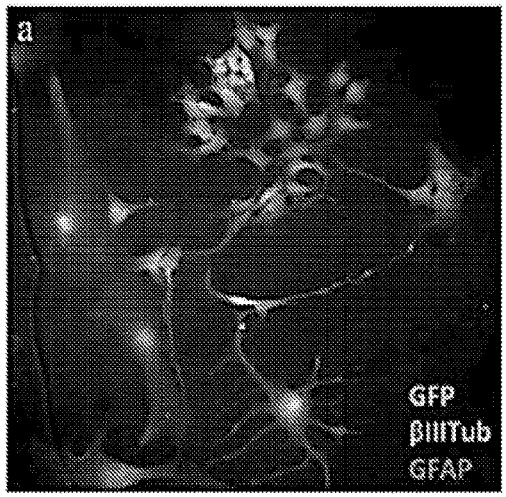
FIG. 5: Multifunctional microspheres are well suited for cell replacement therapies for CNS injury. (A) RG3.6 cells were differentiated in vitro and stained for βIIITub (beta III-tubulin), GFAP (glial fibrillary acidic protein) and GFP (green fluorescent protein). (B) Immunofluorescence of brain sections from animals that received transplants of multifunctional microsphere scaffolds with adhered RG3.6 cells 7 days after traumatic brain injury. Stained for GFP, nestin, and DAPI (4,6-diamidino-2-phenylindole). (C) Sections stained for GFP only. (D) Sections stained for nestin only. (A) taken at 20×, (B-D) at 10× magnification.
Figure 5B:
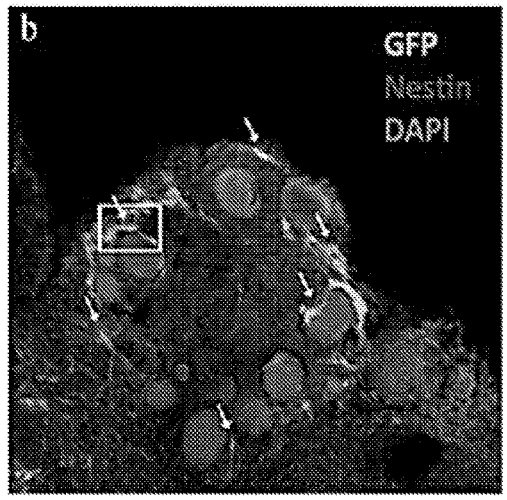
Figure 5C:
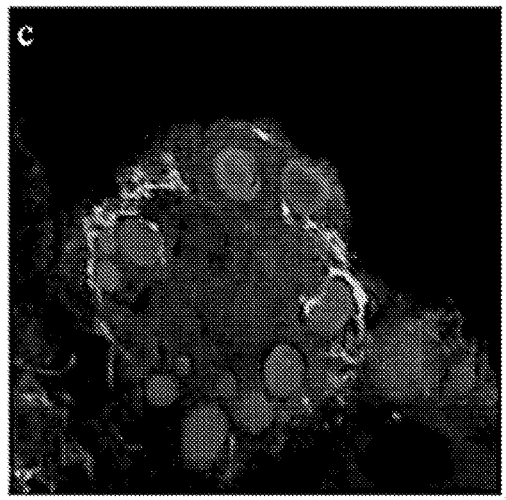
Figure 5D:
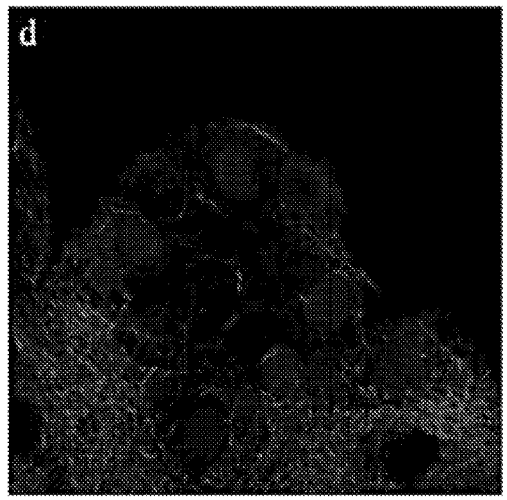
Figure 9:
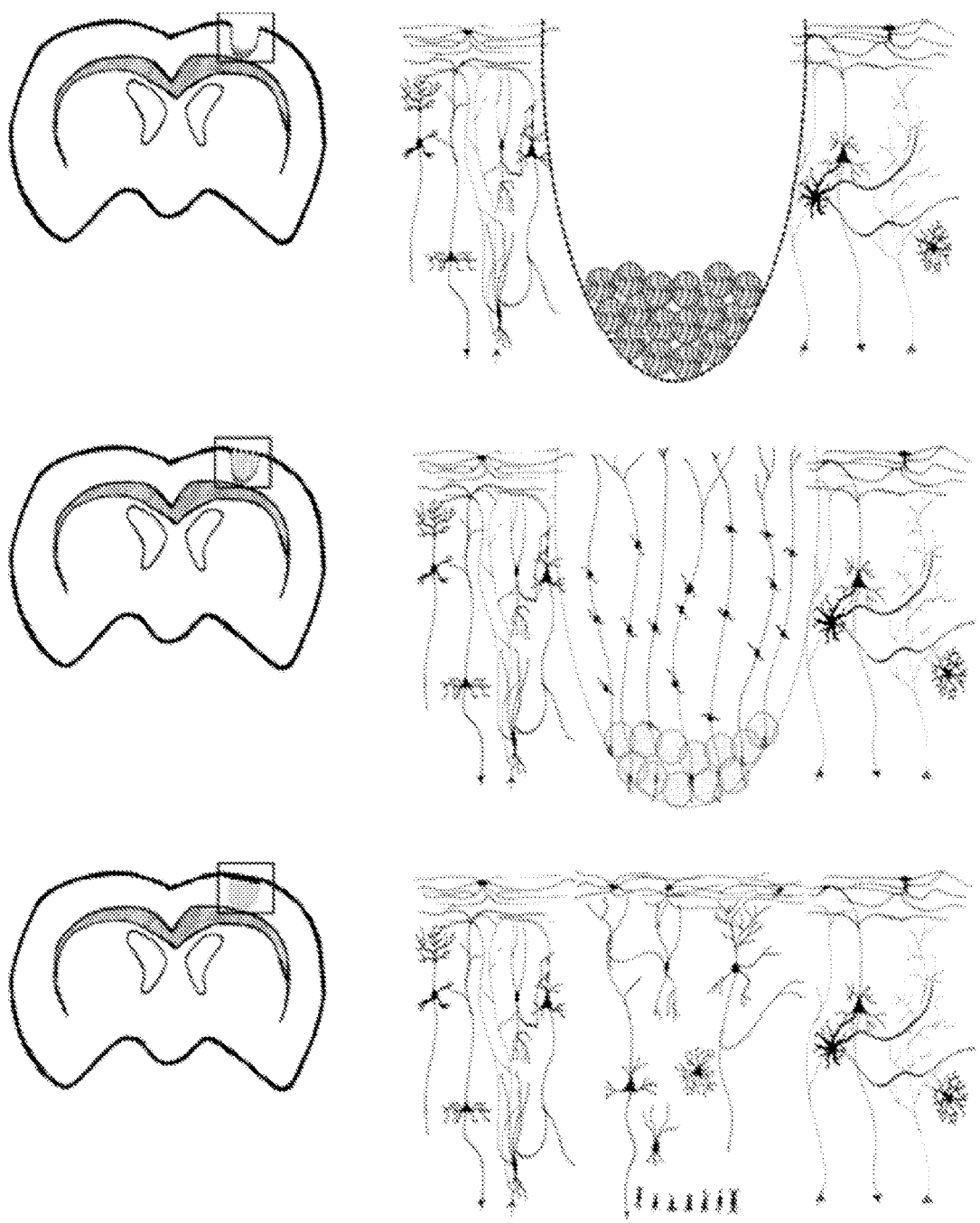
FIG. 9: Schematic representation of the multifunctional scaffold in traumatic brain injury. Coronal illustrations depicting model for brain injury repair (left). Magnified illustrations of boxed inserts provided (right). Top: day 0 green fluorescent protein (GFP)+ventricular zone (VZ) cells injected into lesion cavity on modified chitosan microspheres 7 days post controlled cortical impact. Middle: recapitulation of neurogenesis. GFP+VZ cells proliferate and produce eocortical cells. Spheres degrade. Bottom: microspheres completely degraded; GFP+neurons replace neurons lost from injury.

Stem Cell Engraftment: Numerous studies have encapsulated cells inside spheres or other delivery vehicles to enable the cells to produce soluble growth and trophic factors. In contrast, a delivery vehicle described herein, has the cells adhered to the surface of the microspheres. This configuration enabled the progeny of the stem cells to migrate off of the scaffold into the adjacent tissue, which is crucial to reconstruct a damaged brain. To test this approach, multifunctional microspheres containing the NSC cell line attached to the multifunctional microspheres were transplanted into the lesion cavity at 7 days of recovery from CCI. As the NSCs express GFP they could be distinguished from the host cells using fluorescence microscopy. When the NSCs were differentiated in vitro they formed neurons and glia (see FIG. 5A). At 3 days after transplantation, microspheres could be recognized within the wound cavity adjacent to the host tissue. The NSCs were largely adhered to the beads (see FIGS. 5B and 5C) and they were positive for the stem cell/progenitor marker Nestin (see FIG. 5C). Some of the transplanted cells or their progeny began to migrate from the spheres into the adjacent tissue as shown by arrows in FIG. 5D. These data support the conclusion that the cells thrive on the spheres and withstood the mechanical forces of the syringe. A schematic depicting a method for CNS repair after TBI is provided as FIG. 9.

The initial injury and subsequent inflammation causes a loss of cortical tissue, including a loss of many laminar neurons. After seven days when the inflammation subsides and before the glial scar begins to form, microsphere complexes containing adherent NSC can be transplanted. Ideally, the cells begin to proliferate and form processes that extend to the pial surface, mimicking embryonic neurogensis. Neuroblasts and other progeny can migrate along their processes, ultimately generating neurons appropriate to each cortical layer and supportive glia. Concurrently, the scaffold degrades over time revealing a regenerated, and ordered cortex.

Example 5 (Heparin and Growth Factor Immobilization on the Scaffold)

Ionic and covalent heparin immobilization on chitosan films and microspheres: 2-D chitosan films and 3-D chitosan microspheres were prepared for ionic and covalent heparin immobilization. To prepare chitosan films, 24 well plates were coated with a thin layer of 3% chitosan solution. Wells were allowed to dry overnight and subsequently the acidity was neutralized using 0.5 M sodium hydroxide. Afterwards, plates were rinsed three times with distilled water and incubated overnight with 0.5 mg/mL heparin in HEPES buffered solution (HBS) for ionic binding and in 0.45 mM genipin in HBS for covalent binding. The next day, solutions were aspirated from each well and rinsed three times with HBS. To characterize and compare ionic and covalent immobilization of heparin on the chitosan surfaces, half of the coated wells from each condition were incubated in 1.5 M NaCl for 30 minutes on an orbital shaker at room temperature to remove ionic heparin binding. The remaining wells were incubated in HBS for comparison. Immobilized heparin was detected by the toluidine blue dye. Briefly, a solution of 3 mg/mL toluidine blue was added to each well. After 10 minutes, toluidine blue was removed by aspiration and wells were washed 2 times gently with HBS. Images were acquired with digital color camera (Nikon DS-Ril) and inverted fluorescence microscope (Nikon Ti-S), For 3-D chitosan heparin immobilization, microspheres were prepared as described above and treated as described for 2-D films.

FTIR analysis: The genipin cross-linked chitosan-heparin films were analyzed with Attenuated Total Reflectance Fourier Transform Infrared Spectroscopy (ATR-FTIR; Perkin Elmer) to detect heparin binding. As controls, the chitosan film and heparin powder were measured by FTIR.

Growth factor binding to heparin: The levels of FGF-2 immobilized to chitosan-heparin complexes were evaluated by ELISA. Two dimensional chitosan films were prepared as described above in 96 well plates using 50 μL per well of 3% chitosan. Chitosan coated wells were incubated overnight with HBS only or containing, 0.45 mM genipin, 0.5 mg/mL heparin, or both genipin and heparin. The following day, the wells were aspirated, rinsed three times with fresh HBS and incubated for three hours at room temperature with 100 μL of increasing concentrations of FGF-2 (100, 500, 1,000 ng/mL) or no growth factor. The FGF solutions contained 1 mg/mL BSA to maintain growth factor stability. After allowing the FGF-2 to bind, the solutions were collected in separate eppendorf tubes to determine the unbound FGF-2. Each well was washed gently two times with 50 μL of HBS, which was also added to each respective collection tube. To test long term release, wells were refilled with 100 μL of PBS and collected 7 days later. A sandwich ELISA was used to measure FGF-2 that was released over time. Subtracting the amount released on day 0 from the total amount of FGF-2 added to the scaffold revealed the percentage of bound growth factor.

Figure 3A:
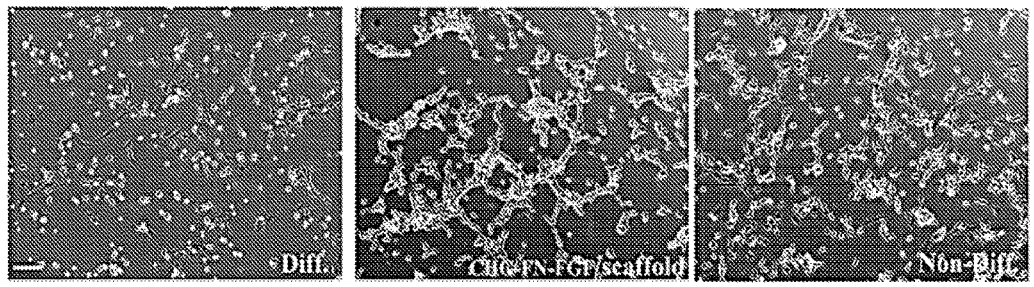
FIG. 3: Effect of immobilized FGF-2 on maintaining stemness and differentiation of NSCs, Primary NSCs were grown in DMEM/F12 supplemented with B27±FGF-2. Dishes were coated with chitosan and fibronectin, with or without heparin-genipin-FGF-2 immobilized (1 μg/ml). Control only received FGF-2 daily. Cells were collected after 4 DIV and analyzed for differentiation. (A) Phase contrast images 20×. (B) Tripotentiality of secondary passaged NSCs differentiated in FGF-2-free media for 7 DIV. (C) Western Blot analysis of differentiation conditions: BLBP: Brain Lipid Binding Protein, TUJ1: Beta III-tubulin, GFAP: Glial Fibrillary Acidic Protein, PCNA: Proliferating Cell Nuclear Antigen, SOX2: SRY-box 2, MAP-2: Microtuble-Associated Protein 2. (D) Graphs represent average IOD (integrated optical density) Scale bar, 100 μm.
Figure 3B:
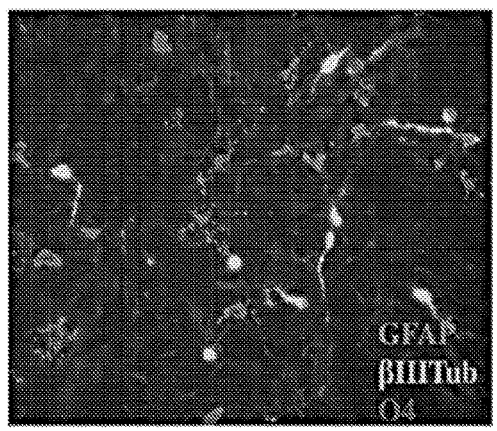
Figure 3C:
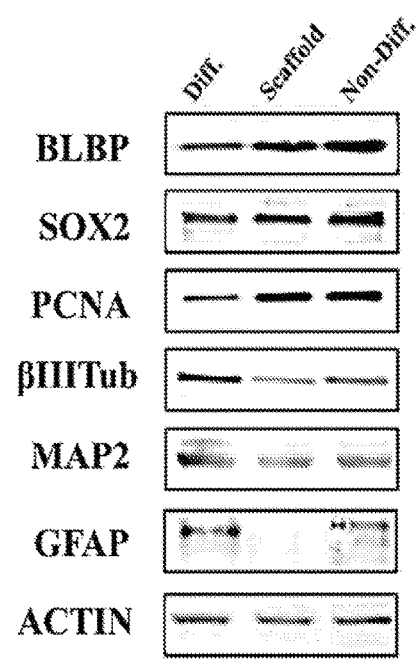
Figure 3D:
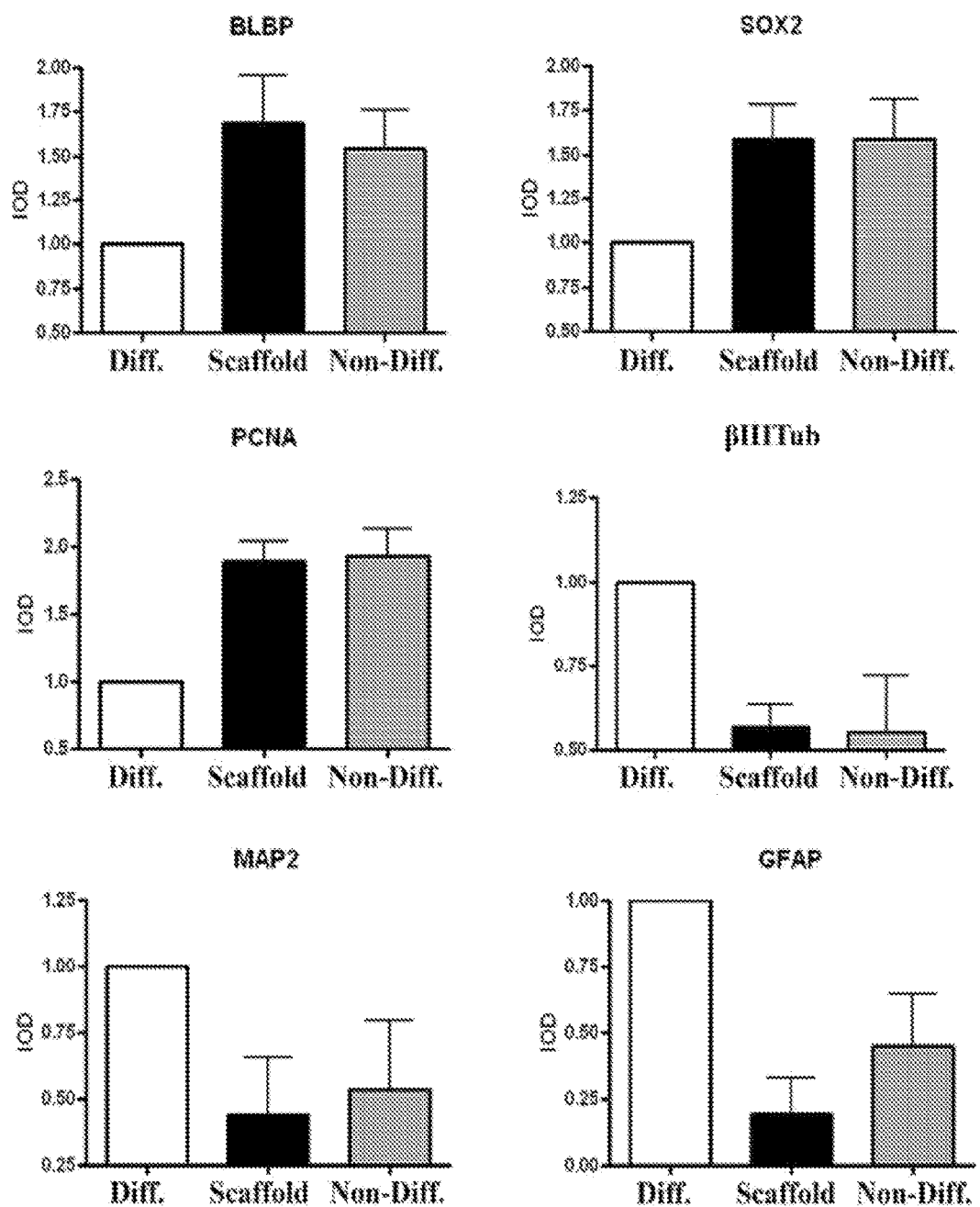

Heparin retention on chitosan: Heparin promotes angiogenesis, has been demonstrated to reduce inflammation and it has high affinity for fibroblast growth factors, thus we reasoned that it would be highly advantageous to covalently attach heparin to the microspheres. FIG. 3A shows the chemical structure of chitosan, heparin, and genipin. Heparin binding to chitosan was tested in two ways, via colorimetric dye staining and FTIR analyses. Positively charged toluidine blue stain, which stains for negatively charged heparin, was strong on chitosan-heparin 2-D films and 3-D microspheres (see FIG. 6B). Toluidine blue also strongly stained the chitosan-heparin-genipin films and microspheres. As expected the control, chitosan alone, did not demonstrate any toluidine blue stain on films and microspheres. The blue staining on the rim of the chitosan alone condition is due to the toluidine blue getting trapped underneath the thin edges of the chitosan coating. This was difficult to avoid, thus, only the center of the films were considered for analyses. When the films or microspheres were immersed and washed in 1.5M NaCl instead of HBS, chitosan alone, as expected, remained unstained. However when the chitosan-heparin films and microspheres (ionic binding) were washed with NaCl followed by toluidine blue, little stain was detected. By contrast, the chitosan-heparin-genipin samples (covalent binding) showed the same positive toluidine blue staining alter the NaCl wash as with HBS (both 2-D and 3-D). This is because the NaCl wash removed the ionic binding between chitosan and heparin, but did not remove the covalent binding between chitosan and heparin when genipin crosslinker was added. The FTIR results confirmed successful immobilization of heparin on the chitosan by genipin cross-linking (0.45 mM). FTIR spectra of genipin cross-linked chitosan-heparin complex exhibited peaks at 1,230 nm and 820 nm, representing S=O and C—O—S stretches of sulfate groups from heparin, respectively (see FIG. 6C). The chitosan-heparin complex also displayed peaks of chitosan functional groups, including N—H bending at 1560 nm and $CH_2$ bending at 1,380 nm. These results demonstrate that 0.45 mM genipin was an appropriate concentration to effectively bind chitosan and heparin. Higher concentrations of genipin (4.5 mM), resulted in extensive cross-linking which eliminated binding sites on the chitosan and heparin; therefore the same sulfate and carboxylate peaks were not seen (data not shown). At lower concentrations of genipin (0.045 mM), insufficient covalent bonds were formed between heparin and chitosan.

FGF-2 Immobilization and Release: Heparin has binding sites for several growth factors, including but not limited to FGFs, VEGF, HGF and BMP. Therefore we investigated the levels of FGF-2 that could be immobilized to chitosan-heparin complexes. Three different concentrations (100, 500, and 1,000 ng/ml) of FGF-2 were evaluated for binding to chitosan-heparin-genipin film scaffolds. As would be predicted, as the concentration of FGF-2 increased, the amount of bound FGF-2 increased (see FIG. 7A). At each concentration approximately 70-80% of the FGF-2 bound to the scaffold (see FIG. 7B). To evaluate the bioactivity of the immobilized FGF-2 a neural stem cell line, RG3.6 cells were seeded onto a 2-D chitosan-heparin-genipin crosslinked scaffold and the MTT assay was performed to assess cell viability and growth after 2 days in vitro. Cells were tested under 4 conditions, they were seeded onto: the complex film with FGF-2 in the medium (Control); onto the complex, film with freshly bound FGF-2 (Bound, Day 0); or onto the complex film where FGF-2 had been bound earlier and incubated at 37° C. for 3 days (Bound Day 3); or onto the complex film without added FGF-2 in the medium. Neural stem cell growth and viability as reflected by the MTT assay was highest on the FGF-2 bound to the scaffold immediately prior to cell seeding. Cell growth on the bound FGF-2 condition was superior to cell growth on the scaffold with FGF-2 provided in the medium. Interestingly, cell growth on the complex film that had immobilized FGF-2 attached to the scaffold three days prior to seeding was comparable to the control, which received FGF-2 added to the media daily (see FIG. 7C). Cell growth on both FGF-2 containing scaffolds, as well as the control was significantly higher than cells grown on the complex film lacking FGF-2 in the medium. When analyzing growth factor release over 1 week (data not shown), a small amount of FGF-2 was detectable through ELISA. However, it is difficult to tell whether the slight decrease in MTT values between the freshly tethered FGF-2 (Day 0) and the FGF-2 bound for 3 days (Day 3), can be attributed to this release or through activity loss. Phase contrast images of the neural stem cells maintained under these growth conditions paralleled the MTT results (FIG. 7D-G).

Example 6 (Comparison of Adhesive Peptides vs. Fibronectin)

Stem Cell Proliferation on Adhesive Peptides: The RGD peptide, first identified in fibronectin, binds to integrin receptors, present on the surface of many types of cells. As reviewed earlier, studies have shown that these receptors are essential for maintaining neural stem cells in a primitive state. Therefore, we hypothesized that the RGD peptide would be sufficient as an adhesive peptide on the scaffold. Confirming the validity of this hypothesis, scaffolds produced with an RGD peptide enhanced the growth of the RG3.6 cells, and when used at an equimolar concentration as fibronectin, produced more robust growth (see FIG. 8).

As we had found that laminin also promoted the growth of neural stells upon the scaffold (see FIG. 1), we tested the small peptide IKVAV, which is the receptor binding peptide present in laminin. Again, at an equimolar concentration to fibronectin, IKVAV promoted superior growth vs, fibronectin (see FIG. 8).

To establish whether these two small peptides might work synergistically we prepared scaffolds that were coated with equimolar concentrations of both RGD and IKVAV. Stem cells plated onto this substrate grew better than those plated onto fibronectin; however, the stem cells did no grow better using both peptides combined vs. using either peptide alone (see FIG. 8)

The description has not attempted to exhaustively enumerate all possible variations. That alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent. Furthermore, all references, publications, U.S. Patents, and U.S. Patent Application Publications cited throughout this specification are hereby incorporated by reference in their entireties as if fully set forth in this specification.

The invention claimed is:

1. A method of culturing stem cells, comprising
preparing a multifunctional matrix by the steps of
   a) drying a chitosan solution to form a chitosan layer;
   b) after step a), attaching a growth factor binding partner to the chitosan layer, wherein the growth factor binding partner is heparin, heparan sulfate or an analogue of heparan sulfate;
   c) after step b), cross-linking the growth factor binding partner to the chitosan layer with genipin;
   d) after step c), applying a solution of one or more growth factors that bind to the growth factor binding partner and can promote growth of the stem cells and allowing the one or more growth factors to attach to the growth factor binding partner such that the one or more growth factors is immobilized; and
   after step d), seeding one or more stem cells onto the multifunctional matrix; and culturing the stem cells thereon.

2. The method of claim 1, wherein preparing a multifunctional matrix further comprises the steps of:
   applying a solution of an adhesive component after step d); and
   allowing the adhesive component to attach to the chitosan layer prior to seeding one or more stem cells onto the multifunctional matrix.

3. The method of claim 1, wherein the growth factor binding partner is heparin.

4. The method of claim 1, wherein stem cells cultured on the multifunctional matrix are in a multipotent and proliferative state free of any soluble growth-promoting proteins.

5. The method of claim 1, wherein stem cells are selected from a group consisting of embryonic stem cells, pluripotential stem cells, somatic stem cells, adipose-derived stem cells, mesenchymal stem cells, hematopoietic stem cells, umbilical cord blood stem cells, oligodendrocyte progenitors, FGF responsive progenitors, induced pluripotential stem cells (iPSCs) and stem cells derived from iPSCs.

6. The method of claim 1, wherein the multifunctional matrix is 2-dimensional and stem cells are selected from hESCs and iPSCs.

7. The method of claim 1, wherein the multifunctional matrix is 3-dimensional.

8. The method of claim 1, wherein the matrix contains xenogeneic free components.

9. The method of claim 5, wherein the stem cells are mammalian cells.

10. The method of claim 1, wherein the one or more growth factors is selected from a group consisting of fibroblast growth factor (FGF), platelet-derived growth factor (PDGF), and heparin-binding epidermal growth factor (Hb-EGF).

11. The method of claim 10, wherein FGF is FGF-2.

12. The method of claim 2, wherein the adhesive component is an extracellular matrix protein selected from a group consisting of Fibronectin, Laminin, Vitronectin, Fibrillin, Fibrinogen, Plasminogen, Plasmin, Aggrecan, Brevican, Tenascin, Collagen, Elastin, Hyaluronic acid proteoglycan, Keratan sulfate proteoglycan, Heparan sulfate proteoglycan, Chondroitin sulfate proteoglycan, Syndecan-1 (proteoglycan), and IGF Binding Protein.

13. The method of claim 2, wherein the adhesive component is an extracellular matrix peptide having a peptide sequence comprising RGD or IKVAV.

14. The method of claim 1, wherein the growth factor binding partner is heparin and the one or more growth factors is FGF.

15. The method of claim 9, wherein the mammalian cells are rodent, primate or human cells.

16. The method of claim 1, wherein the one or more growth factors comprises one or more of FGF, Hb-EGF and PDGF.

17. The method of claim 16, wherein the one or more growth factors comprises a combination of Hb-EGF and FGF-2.

18. The method of claim 16, wherein the one or more growth factors comprises a combination of PDGF and FGF-2.

19. The method of claim 16, wherein the one or more growth factors comprises a combination of FGF, Hb-EGF and PDGF.

* * * * *